US010428371B2

(12) United States Patent
Hanami et al.

(10) Patent No.: US 10,428,371 B2
(45) Date of Patent: Oct. 1, 2019

(54) FLUORESCENT LABELED SINGLE-STRANDED NUCLEIC ACID AND USE THEREOF

(71) Applicant: KABUSHIKI KAISHA DNAFORM, Yokohama-shi, Kanagawa (JP)

(72) Inventors: Takeshi Hanami, Saitama (JP); Yoshihide Hayashizaki, Saitama (JP); Takahiro Soma, Saitama (JP); Yasumasa Kimura, Kanagawa (JP)

(73) Assignee: KABUSHIKI KAISHA DNAFORM, Kanagawa (JP)

( * ) Notice: Subject to any disclaimer, the term of this patent is extended or adjusted under 35 U.S.C. 154(b) by 0 days.

(21) Appl. No.: 15/300,183

(22) PCT Filed: Mar. 27, 2015

(86) PCT No.: PCT/JP2015/059550
§ 371 (c)(1),
(2) Date: Sep. 28, 2016

(87) PCT Pub. No.: WO2015/152024
PCT Pub. Date: Oct. 8, 2015

(65) Prior Publication Data
US 2017/0145482 A1 May 25, 2017

(30) Foreign Application Priority Data

Mar. 31, 2014 (JP) .................. 2014-072280

(51) Int. Cl.
*C12Q 1/68* (2018.01)
*C12Q 1/6818* (2018.01)
*C12Q 1/6816* (2018.01)
*C09B 23/04* (2006.01)
*C09B 23/06* (2006.01)

(52) U.S. Cl.
CPC ............ *C12Q 1/6818* (2013.01); *C09B 23/04* (2013.01); *C09B 23/06* (2013.01); *C12Q 1/6816* (2013.01)

(58) Field of Classification Search
CPC .................................................. C12Q 1/6818
USPC ................... 536/23.1, 26.6; 435/6.1
See application file for complete search history.

(56) References Cited

U.S. PATENT DOCUMENTS

| 5,455,166 A | 10/1995 | Walker |
| 5,554,517 A | 9/1996 | Davey et al. |
| 5,824,517 A | 10/1998 | Cleuziat et al. |
| 5,846,726 A | 12/1998 | Nadeau et al. |
| 5,919,630 A | 7/1999 | Nadeau et al. |
| 6,054,279 A | 4/2000 | Nadeau et al. |
| 6,410,278 B1 | 6/2002 | Notomi et al. |
| 6,951,722 B2 | 10/2005 | Mukai et al. |
| 7,273,700 B2 | 9/2007 | Kurane et al. |
| 8,067,162 B2 | 11/2011 | Hayashizaki et al. |
| 8,383,792 B2 | 2/2013 | Okamoto et al. |
| 2005/0048485 A1 | 3/2005 | Kirane et al. |
| 2006/0160084 A1 | 7/2006 | Mitani et al. |
| 2007/0190531 A1 | 8/2007 | Mitani et al. |
| 2008/0227104 A1 | 9/2008 | Hayashizaki et al. |
| 2010/0092971 A1 | 4/2010 | Okamoto |
| 2011/0281266 A1 | 11/2011 | Sergeev et al. |

FOREIGN PATENT DOCUMENTS

| EP | 1 970 453 | 9/2008 |
| JP | 7-114718 | 12/1995 |
| JP | 2650159 B | 5/1997 |
| JP | 2710159 B | 10/1997 |
| JP | 11-123083 | 5/1999 |
| JP | 3867926 B | 10/2006 |
| JP | 3942627 B | 4/2007 |
| JP | 2009-171935 | 8/2009 |
| JP | 2013-183736 | 9/2013 |
| WO | 87/06270 | 10/1987 |
| WO | 95/25180 | 9/1995 |
| WO | 99/09211 | 2/1999 |

(Continued)

OTHER PUBLICATIONS

Okamoto et al. "A nucleic acid probe labeled with desmethyl thiazole orange: a new type of hybridization-sensitive fluorescent oligonucleotide for live-cell RNA imaging" Organic & Biomolecular Chemistry, vol. 11, p. 362-371. (Year: 2013).*
Tyagi et al., "Molecular Beacons: Probes that Fluoresce upon Hybridization", Nat. Biotechnol., 1996, vol. 14, pp. 303-308.
Ikeda et al., "Sequence Dependence of Fluorescence Emission and Quenching of Doubly Thiazole Orange Labeled DNA: Effective Design of a Hybridization-Sensitive Probe", Bioconjugate Chem., 2008, vol. 19, pp. 1719-1725.
Ikeda et al., "Exciton-Controlled Hybridization-Sensitive Fluorescent Probes: Multicolor Detection of Nucleic Acids", Angew. Chem. Int. Ed. Engl., 2009, vol. 48, pp. 6480-6484.

(Continued)

*Primary Examiner* — Jezia Riley
(74) *Attorney, Agent, or Firm* — Hamre, Schumann, Mueller & Larson, P.C.

(57) ABSTRACT

The present invention is intended to provide a novel fluorescent labeled single-stranded nucleic acid, by which the background of an exciton oligomer can be further reduced and the novel use thereof. The present invention relates to a labeled single-stranded nucleic acid having at least two fluorescent atomic group pairs that exhibit an exciton effect. The labeled single-stranded nucleic acid is characterized in that the emission peak wavelength of one of the fluorescent atomic group pairs (fluorescent atomic group pair A) is shorter than the excitation peak wavelength of the other fluorescent atomic group pair (fluorescent atomic group pair B), and the fluorescent atomic group pairs A and B have a Förster resonance energy transfer (FRET) effect. This fluorescent labeled single-stranded nucleic acid is usable as a primer for amplifying a target nucleic acid or a probe to be hybridized with a target nucleic acid.

9 Claims, 4 Drawing Sheets
Specification includes a Sequence Listing.

(56) References Cited

FOREIGN PATENT DOCUMENTS

| WO | 00/28082 | 5/2000 |
|----|----------|--------|
| WO | 02/16639 | 2/2002 |
| WO | 02/077224 | 10/2002 |
| WO | 2008/111485 | 9/2008 |

OTHER PUBLICATIONS

Ikeda et al., "Doubly thiazole orange-labeled cytidine for functional expansion of a hybridization-sensitive probe", Tetrahedron Letters 50, 2009, vol. 51, pp. 7191-7195.

Hanami et al., "Eprobe Mediated Real-Time PCR Monitoring and Melting Curve Analysis", PLOS ONE, 2013, vol. 8, Issue 8, e70942.

Mitani et al., "Rapid SNP diagnostics using asymmetric isothermal amplification and a new mismatchsuppression technology", Nature Methods, 2007, vol. 4, No. 3, pp. 257-262.

Parkhurst et al., "Kinetic Studies by Fluorescence Resonance Energy Transfer Employing a Double-Labeled Oligonucleotide: Hybridization to the Oligonucleotide Complement and to Single-Stranded DNA", Biochemistry, 1995, vol. 34, No. 1, pp. 285-292.

Extended European Search Report for the corresponding European Patent Application No. 15773110.0, dated Nov. 14, 2017, 9 pages.

Okamoto et al., "A nucleic acid probe labeled with desmethyl thiazole orange: a new type of hybridization-sensitive fluorescent oligonucleotide for live-cell RNA imaging", Organic & Biomolecular Chemistry, vol. 11, No. 2, pp. 362-371, Jan. 2014.

Enokida et al., "Rapid Detection of SNP (c.309T>G) in the MDM2 Gene by the Duplex SmartAmp Method", PLOS ONE, vol. 8, Issue 4, p. e60151 (1-10), Apr. 2013.

Robertson et al., "Fluorescent PNA Probes as Hybridization Labels for Biological RNA", Biochemistry, vol. 45, No. 19, pp. 6066-6074, May 2006.

Office Action in the corresponding Japanese Patent Application (No. 2016-511609) dated Dec. 18, 2018.

Ikeda et al., "Emission control by binary energy transfer processes onoligouridine", Organic & Biomolecular Chemistry, 2011, vol. 9, pp. 6598-6603.

Okamoto et al., "Design of binary energy transfer on nucleic acids", Photomedicine & Photobiology, 2011, vol. 33, pp. 45-46.

* cited by examiner

FLUORESCENT LABELED SINGLE-STRANDED NUCLEIC ACID AND USE THEREOF

TECHNICAL FIELD

The present invention relates to a fluorescent labeled single-stranded nucleic acid and the use thereof. In particular, the present invention relates to a fluorescent labeled single-stranded nucleic acid capable of reducing a fluorescent background and the use thereof.

CROSS-REFERENCE TO RELATED APPLICATION

This application claims priority from Japanese Patent Application No. 2014-72280 filed on Mar. 31, 2014, the entire subject matters of which are incorporated herein by reference.

BACKGROUND ART

In analysis of biological phenomena of cells and diagnoses of disease factors, detections and diagnoses at the molecular level have been required. In order to achieve this, it is required to detect a specific protein and a specific nucleic acid sequence, and the fluorescence has been widely used for the detection. Specifically, a method using a fluorescent substance that increases the fluorescence intensity by binding to a target substance such as a target protein or a target nucleic acid sequence has been known. As the fluorescent substance, for example, a substance that exhibits a Förster (fluorescence) resonance energy transfer (FRET) effect or a substance that emits fluorescence by being irradiated with excitation light has been used.

For example, in the Molecular Beacon method described in Non-Patent Literature 1, a nucleic acid in which different respective dyes have been introduced into the 5'-end and the 3'-end of a nucleic acid sequence which independently forms a step-loop structure is used. The fluorescence is quenched by the FRET effect at the time of no hybridization, and the fluorescence is emitted when a specific hybridization occurs. This method has limitations that the sequence is required to form a stem-loop structure, and the fluorescent dyes are required to be introduced into the respective ends.

As a different quenching mechanism as a substitute for the conventional technology, a method employing an exciton effect exhibited when at least two dye molecules are aggregated in parallel has been proposed (Non-Patent Literatures 2 to 5, Patent Literature 1). This is a method using a complex labeling substance having, in the same molecule, chemical structures of at least two dye molecules that do not emit fluorescence by an exciton effect in the single strand state and emit fluorescence by resolving the aggregation state at the time when these molecules are intercalated into or groove-bound to a nucleic acid.

A primer or probe (also called an exciton oligomer) obtained by introducing this labeling substance into oligonucleotide can be used in amplification or detection of a target nucleic acid. This exciton oligomer or the like allows fluorescent switching before and after hybridization with only one type of dye, and in the case where the exciton oligomer is used for real-time monitoring of amplification reaction, it gives a sequence specific fluorescent signal. Thus, the conventional problem that non-specific amplification is also detected when an intercalator such as SYBR green I is used can be overcome. Furthermore, since a fluorophore can be introduced into dT or dC, the sequence is barely restricted.

Patent Literature 1: JP 2009-171935 A (Japanese Patent No. 4370385)
Patent Literature 2: JP 2013-183736 A
The entire subject matters of which are incorporated herein by reference.

Non-Patent Literature 1: Tyagi, S., Kramer, F. R. (1996) Nat. Biotechnol. 14, 303-308.
Non-Patent Literature 2: Ikeda S, Kubota T, Kino K, Okamoto A., Bioconjug Chem. 2008. 19. 1719-1725.
Non-Patent Literature 3: Ikeda S, Kubota T, Yuki M, Okamoto A., Angew Chem Int Ed Engl. 2009. 48. 6480-6484.
Non-Patent Literature 4: Ikeda S, Yuki M, Yanagisawa H, Okamoto A., Tetrahedron Lett. 2009, 51, 7191-7195
Non-Patent Literature 5: Takeshi Hanami, Diane Delobel, Hajime Kanamori, Yuki Tanaka, Yasumasa Kimura, Ayako Nakasone, Takahiro Soma, Yoshihide Hayashizaki, Kengo Usui, Matthias Harbers, PLOS ONE, August 2013, volume 8, Issue 8, e70942
The entire subject matters of which are incorporated herein by reference.

SUMMARY OF INVENTION

Problem to be Solved by the Invention

It turned out by the studies carried out by the inventors of the present invention that even using the exciton oligomer, a certain background is present in measurement with high sensitivity. It also turned out that this background interferes fluorescence detection in a method for detecting fluorescence that is slightly generated at the time when the exciton oligomer used as a probe is bound to a fine amount of target.

Hence, the present invention is intended to provide a novel fluorescent labeled single-stranded nucleic acid, by which the background of an exciton oligomer can be further reduced and the novel use thereof.

The conventional exciton oligomer is a labeled single-stranded nucleic acid into which two fluorescent dyes (thiazole orange and a similar substance thereof) have been introduced. The exciton oligomer hardly emits fluorescence by the exciton effect obtained when two fluorescent dyes form exciplex in the single strand state. However, for example, the exciton oligomer has a property of fluorescent switching where when it hybridizes to a target DNA, two dyes are apart from each other, and the exciton effect is resolved, and thus, fluorescence which is originally in the fluorescent dyes is emitted.

However, as a result of the studies by the inventors of the present invention, it was found that the fluorescence quenching mechanism by the exciton effect is not perfect, the fluorescence originally in the fluorescent dyes cannot be completely quenched. Thus, the background derived from the fluorescence in the single strand state is considerably present. Hence, the inventors of the present invention further conducted studies aimed at a further reduction in background fluorescence. As the results of the studies, they found that the background fluorescence can be further reduced by combining the fluorescence switching caused by the exciton effect and the FRET effect and completed the present invention.

Means for Solving Problem

The present invention is as follows.

(Supplementary Note 1) A labeled single-stranded nucleic acid having at least two fluorescent atomic group pairs that exhibit an exciton effect, wherein an emission peak wavelength of one of the fluorescent atomic group pairs (hereinafter referred to as the fluorescent atomic group pair A) is shorter than an excitation peak wavelength of the other fluorescent atomic group pair (hereinafter referred to as the fluorescent atomic group pair B), and the fluorescent atomic group pairs A and B have a Förster resonance energy transfer (FRET) effect.

(Supplementary Note 2) The labeled single-stranded nuclei acid according to Supplementary Note 1, wherein a base having the fluorescent atomic group pair A and a base having the fluorescent atomic group pair B are contained in the labeled single-stranded nucleic acid at a distance at which the fluorescent atomic group pairs A and B have an FRET effect.

(Supplementary Note 3) The labeled single-stranded nucleic acid according to Supplementary Note 2, wherein the distance between the base having the fluorescent atomic group pair A and the base having the fluorescent atomic group pair B is 1 to 11 bases.

(Supplementary Note 4) The labeled single-stranded nucleic acid according to any one of Supplementary Notes 1 to 3, wherein the base having the fluorescent atomic group pair that exhibits an exciton effect has a structure represented by the following formula (16), (16b), (17), or (17b):

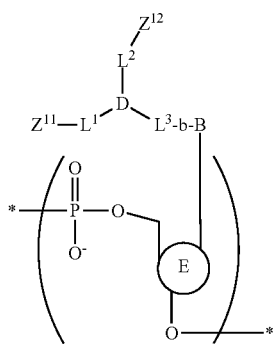

(16)

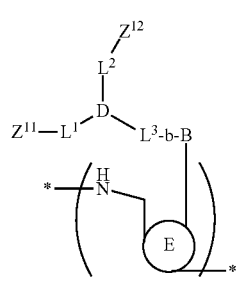

(16b)

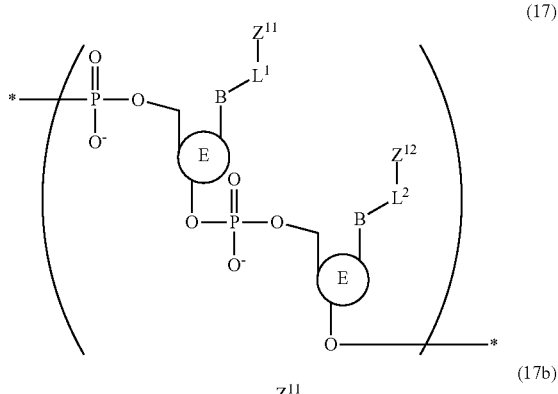

(17)

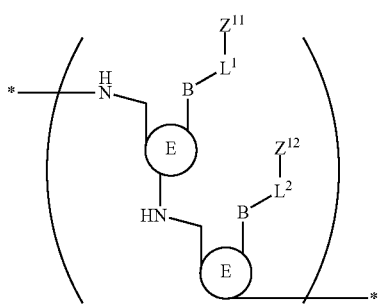

(17b)

where in the formulae (16), (16b), (17), and (17b),

B is an atomic group having a natural nucleobase (adenine, guanine, cytosine, thymine, or uracil) skeleton or an artificial nucleobase skeleton, E is:
(i) an atomic group having a deoxyribose skeleton, a ribose skeleton, or a structure derived from either one of them, or
(ii) an atomic group having a peptide structure or a peptoid structure, $Z^{11}$ and $Z^{12}$ are each a fluorescent atomic group that exhibits an exciton effect, and may be identical to or different from each other, $L^1$, $L^2$, and $L^3$ are each a linker (a linking atom or a linking atomic group), have each any main chain length (the number of main chain atoms), each may or may not contain each of C, N, O, S, P, and Si in the main chain, each may or may not contain each of a single bond, a double bond, a triple bond, an amide bond, an ester bond, a disulfide bond, an imino group, an ether bond, a thioether bond, and a thioester bond in the main chain, and may be identical to or different from each other, D is CR, N, P, P=O, B, or SiR where R is a hydrogen atom, an alkyl group, or any substituent, and b is a single bond, a double bond, or a triple bond, or alternatively, in the formulae (16) and (16b), $L^1$ and $L^2$ are each a linker, $L^3$, D, and b may not be present, and $L^1$ and $L^2$ may be bound directly to B, provided that:

in the formulae (16) and (17), E is an atomic group described in the item (i), and at least one O atom in a phosphoric acid linkage may be substituted with an S atom;

in the formulae (16b) and (17b), E is an atomic group described in the item (ii); and in the formulae (17) and (17b), the respective Bs may be identical to or different from each other, and the respective Es may be identical to or different from each other.

(Supplementary Note 5) The labeled single-stranded nucleic acid according to Supplementary Note 4, wherein the structure represented by the formula (16) is a structure represented by the following formula (16-1) or (16-2), the structure represented by the formula (16b) is a structure represented by the following formula (16b-1) or (16b-2), the structure represented by the formula (17) is a structure represented by the following formula (17-1), and the structure represented by the formula (17b) is a structure represented by the following formula (17b-1):

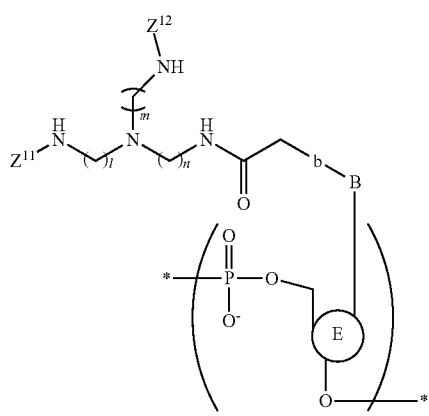

(16-1)

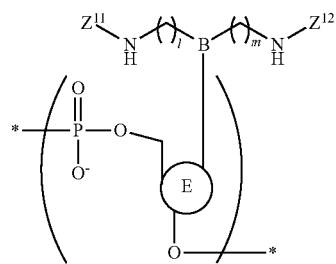

(16-2)

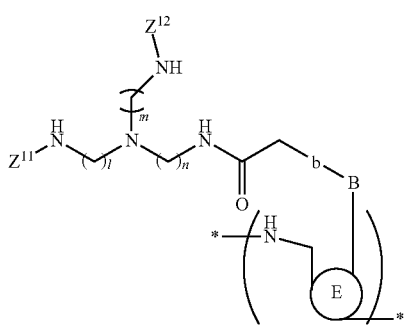

(16b-1)

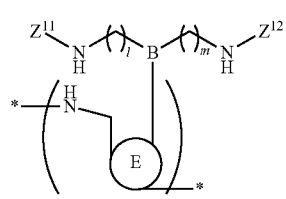

(16b-2)

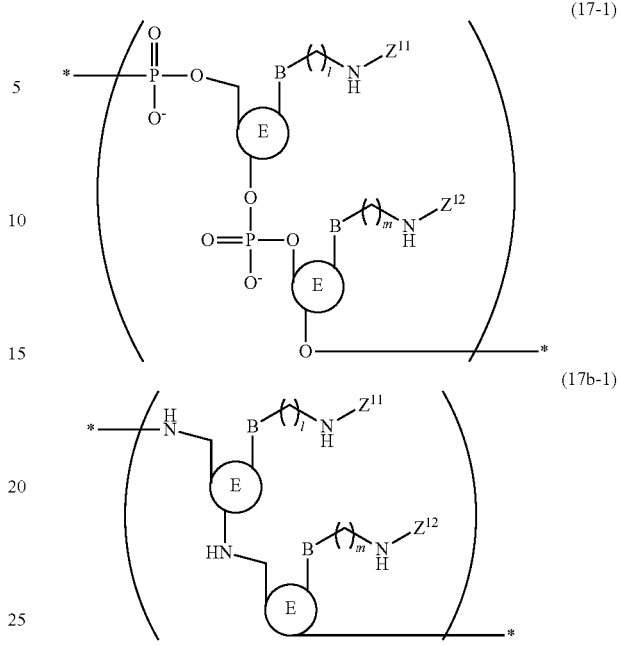

(17-1)

(17b-1)

where in the formulae (16-1), (16-2), (16b-1), (16b-2), (17-1), and (17b-1), l, m and n are any positive integers, may be identical to or different from each other, each may or may not contain each of C, N, O, S, P, and Si in a main chain thereof, and each may or may not contain each of a single bond, a double bond, a triple bond, an amide bond, an ester bond, a disulfide bond, an imino group, an ether bond, a thioether bond, and a thioester bond in the main chain, B, E, $Z^{11}$, $Z^{12}$, and b are identical to those in the formulae (16), (16b), (17), and (17b), and in the formulae (16-1), (16-2), and (17-1), at least one O atom in a phosphoric acid linkage may be substituted with an S atom.

(Supplementary Note 6) The labeled single-stranded nucleic acid according to Supplementary Note 4 or 5, wherein the base having the fluorescent atomic group pair that exhibits an exciton effect has a structure represented by the formula (16).

(Supplementary Note 7) The labeled single-stranded nucleic acid according to any one of Supplementary Notes 4 to 6, wherein $Z^{11}$ and $Z^{12}$ are each independently an atomic group represented by any one of the following formulae (7) to (10):

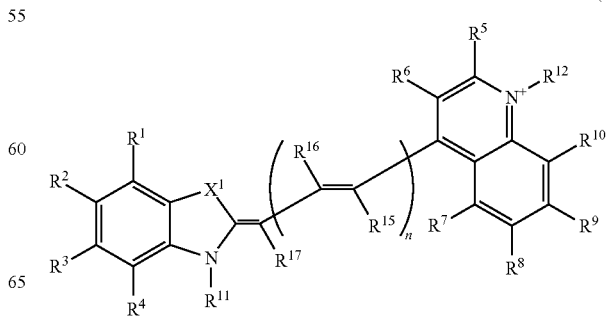

(7)

-continued

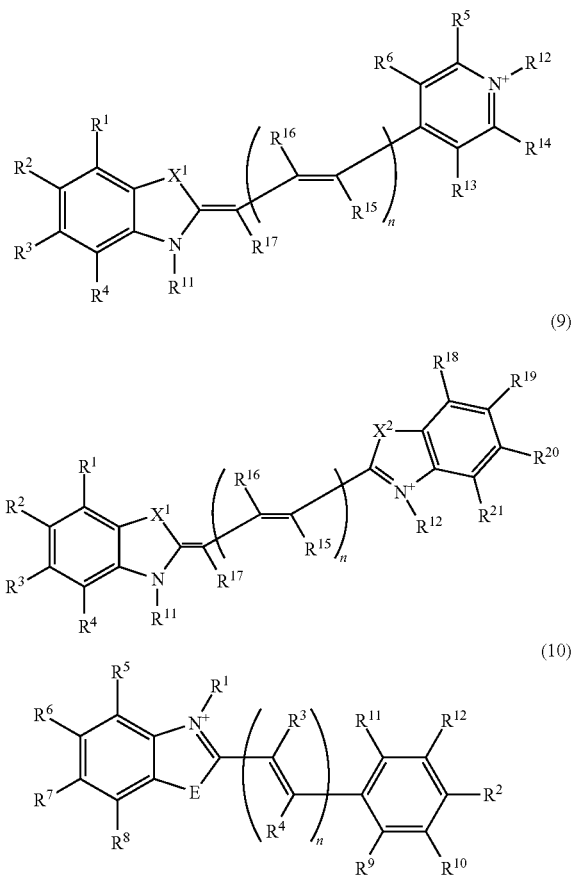

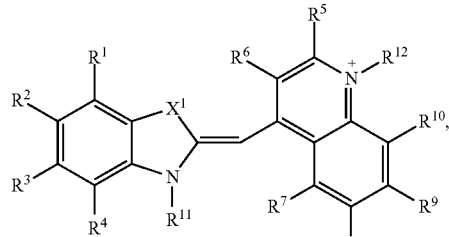

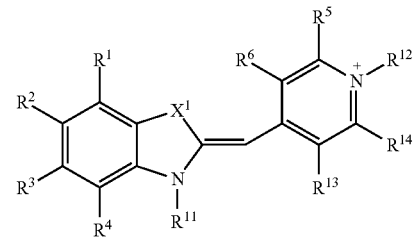

where in the formulae (7) to (9), $X^1$ and $X^2$ are S or O n is 0 or a positive integer, $R^1$ to $R^{10}$ and $R^{13}$ to $R^{21}$ are each independently a hydrogen atom, a halogen atom, a lower alkyl group, a lower alkoxy group, a nitro group, or an amino group, one of $R^{11}$ and $R^{12}$ is a linking group to be bound to $L^1$ or $L^2$ in the formulae (16), (17), (16b), and (17b), and the other is a hydrogen atom or a lower alkyl group, when a plurality of $R^{15}$s are present in the formula (7), (8), or (9), they may be identical to or different from each other, when a plurality of $R^{16}$s are present in the formula (7), (8), or (9), they may be identical to or different from each other, and $X^1$, $X^2$, and $R^1$ to $R^{21}$ in $Z^{11}$ and $X^1$, $X^2$, and $R^1$ to $R^{21}$ in $Z^{12}$ may be identical to or different from each other, respectively, and where in the formula (10), E
is S or O, $R^2$ to $R^{12}$ are each independently a hydrogen atom, a halogen atom, a lower alkyl group, a lower alkoxy group, a nitro group, or an amino group, $R^1$ is a linking group to be bound to $L^1$ or $L^2$ in the formulae (16), (17), (16b), and (17b), when a plurality of $R^3$s is present in the formula (10), they may be identical to or different from each other, and when a plurality of $R^4$s is present in the formula (10), they may be identical to or different from each other.

(Supplementary Note 8) The labeled single-stranded nucleic acid according to Supplementary Note 7, wherein $Z^{11}$ and $Z^{12}$ are each independently an atomic group represented by the formula (7) or (8), and $Z^{11}$ and $Z^{12}$ represented by the formula (7) or (8) are each a group represented by the following formula (19) or (20):

where in the formulae (19) and (20), $X^1$, $R^1$ to $R^{10}$, $R^{13}$ and $R^{14}$, $R^{11}$, and $R^{12}$ are identical to those in the formulae (7) to (9).

(Supplementary Note 9) The labeled single-stranded nucleic acid according to any one of Supplementary Notes 1 to 8, used as a primer for amplifying a target nucleic acid or a probe to be hybridized with a target nucleic acid.

(Supplementary Note 10) A method for detecting a target nucleic acid, including measuring fluorescence under the conditions where the labeled single-stranded nucleic acid according to any one of Supplementary Notes 1 to 8 as a probe is capable of hybridizing with a target nucleic acid, to determine the presence or absence of the hybridization of the target nucleic acid to the probe.

(Supplementary Note 11) A method for amplifying a target nucleic acid, including amplifying a target nucleic acid using the labeled single-stranded nucleic acid according to any one of Supplementary Notes 1 to 8 as a primer.

Effects of the Invention

The present invention can provide a labeled single-stranded nucleic acid having exciton oligomer as a basic skeleton, capable of further reducing the background fluorescence.

DESCRIPTION OF EMBODIMENTS

<Labeled Single-Stranded Nucleic Acid>

Figure 1A:
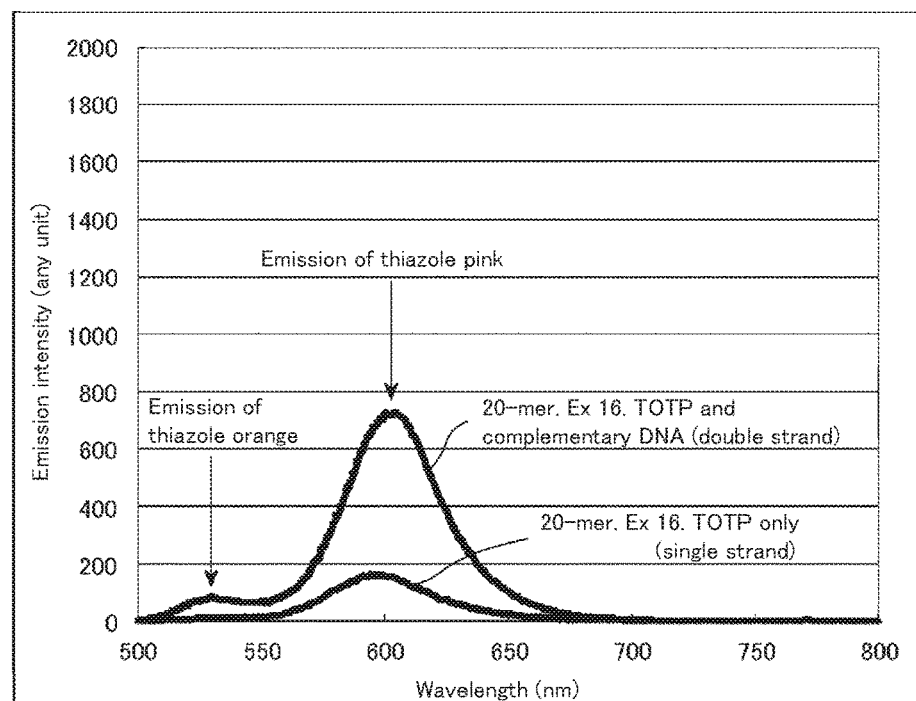
FIG. 1A shows a result of spectrum measurement of a fluorescence nucleic acid probe of the present invention into which two fluorescent dyes having an exciton effect have been introduced, obtained in Example 1. This result was obtained using oligonucleotide (EX16-12TOTP) having thiazole pink (TP) at the 12th base from the 3' end and thiazole orange (TO) at the 16th base from the 3' end.

The present invention is a labeled single-stranded nucleic acid having at least two fluorescent atomic group pairs that exhibit an exciton effect. This labeled single-stranded nucleic acid of the present invention is characterized in that:

(a) the emission peak wavelength of one of the fluorescent atomic group pairs (the fluorescent atomic group pair A) is shorter than the excitation peak wavelength of the other fluorescent atomic group pair (the fluorescent atomic group pair B), and (b) the fluorescent atomic group pairs A and B have a Förster resonance energy transfer (FRET) effect.

A fluorescent atomic group pair that exhibits an exciton effect and a labeled single-stranded nucleic acid having the fluorescent atomic group pair that exhibits an exciton effect are described in Patent Literatures 1 and 2 and Non-Patent Literatures 2 to 5. However, the labeled single-stranded nucleic acid having at least two fluorescent atomic group pairs, having the characteristics (a) and (b), is not described in any of Patent Literatures 1 and 2 and Non-Patent Literatures 2 to 5.

The labeled single-stranded nucleic acid of the present invention is a single-stranded nucleic acid having at least two fluorescent atomic group pairs that exhibit an exciton effect.

The single-stranded nucleic acid can be DNA or RNA or a mixture thereof and can further be a nucleic acid in which some or all of nucleic acid bases are non-natural nucleic acid bases. The labeled single-stranded nucleic acid of the present invention may partially have a double-stranded structure as long as being capable of hybridizing with a target nucleic acid. This is described in further detail below.

The base length of the labeled single-stranded nucleic acid is not limited to particular base lengths. However, for the reason that the labeled single-stranded nucleic acid is mainly used as a probe or a primer and further is a single-stranded nucleic acid having at least two fluorescent atomic group pairs that exhibit an exciton effect and satisfies the characteristic (b), the base length of the single-stranded nucleic acid is, for example, in the range from 4- to 100-mer, preferably from 10- to 50-mer, more preferably, from 10- to 40-mer, yet more preferably from 10- to 30-mer. The base length is selected, as appropriate, by the use of the labeled single-stranded nucleic acid. For example, in the case where the labeled single-stranded nucleic acid is used for a capture of mRNA, a single-stranded nucleic acid having a base length of about 80-mer is favorably used, in the case where the labeled single-stranded nucleic acid is used as a PCR primer, a single-stranded nucleic acid having a base length of about 40-mer is favorably used, and in the case where the labeled single-stranded nucleic acid is used as a probe, a single-stranded nucleic acid having a base length of about 30-mer is favorably used.

The number of the fluorescent atomic group pairs that exhibit an exciton effect in the labeled single-stranded nucleic acid is at least two and can also be three or more. In order to exhibit an FRET effect, the number of fluorescent atomic group pairs that exhibit an exciton effect is practically only necessary to be two. However, considering the use of the labeled single-stranded nucleic acid, the kind of the fluorescent atomic groups, the distance between the fluorescent atomic group pairs, and the extent of the FRET effect, the number may be three and may also be four or more.

According to the exciton effect, for example, the fluorescence intensity in a single strand state is suppressed and thereby allows a double helix structure to be detected further effectively. The exciton effect (exciton coupling) is an effect in which, for example, a plurality of dyes aggregate in parallel to form an H-aggregate and thereby hardly exhibit fluorescence emission. Conceivably, this effect is obtained as follows. That is, the excitation state of the dye is split into two energy levels by Davydov splitting, excitation to the higher energy level and then internal conversion into the lower energy level occur, and thereby the emission is thermodynamically forbidden. However, these descriptions do not limit the present invention by any means. The possible occurrence of the exciton effect can be confirmed by the appearance of the absorption band of the dyes that have formed the H-aggregate, in a shorter wavelength as compared to the absorption band of a single dye. Examples of the dyes that exhibit such an effect include thiazole orange and derivatives thereof, thiazole pink and derivatives thereof, oxazole yellow and derivatives thereof, cyanine and derivatives thereof, hemicyanine and derivatives thereof, and methyl red and derivatives thereof, as well as dye groups generally referred to as cyanine dyes and azo dyes.

These dyes are easily bound to a DNA-DNA double strand and a DNA-RNA double strand each of which forms a double helix or a double strand formed of an artificial nucleic acid such as phosphorothioate nucleic acid, PNA (peptide nucleic acid), or locked nucleic acid (LNA) (BNA) with DNA or RNA by intercalation. When a plurality of such dyes has been introduced into a single-stranded nucleic acid, strong quenching occurs in the general single strand state (for example, the state of only a probe or a primer before hybridization). When the single-stranded nucleic acid hybridizes with a target DNA or RNA, the aggregate is resolved, and the dyes are individually intercalated into the double strand. At that time, there is no electronic interaction between the dyes, thereby exhibiting no exciton effect and exhibiting intense fluorescence emission. The absorption band of the dyes at that time is the same as the absorption band of the single dye, and this demonstrates that the exciton effect is not exhibited between the dyes. When the dyes are intercalated into a double strand, the twist on the structure originally in the dyes is resolved, and thus, the fluorescence emission becomes further intense.

Characteristic (a)

The emission peak wavelength(s) of one of the fluorescent atomic group pairs (the fluorescent atomic group pair A) is shorter than an excitation peak wavelength(s) of the other fluorescent atomic group pair (the fluorescent atomic group pair B). The emission peak wavelength means a peak wavelength of emission spectrum generated at the time when the fluorescent atomic group pair A is irradiated with excitation light and changes according to the types of fluorescent atomic groups of the fluorescent atomic group pair A. The excitation peak wavelength means a peak wavelength of spectrum of excitation light that can be absorbed by the fluorescent atomic group pair B and changes according to the types of fluorescent atomic groups of the fluorescent atomic group pair B. The emission peak wavelength(s) of the fluorescent atomic group pair A and the excitation peak wavelength(s) of the fluorescent atomic group pair B are not limited. Note here that when the labeled single-stranded nucleic acid of the present invention is used as a probe or a primer, and a fluorescent label is used for detection, fluorescence is emitted from the fluorescent atomic groups of the fluorescent atomic group pair B, and thus, fluorescent atomic groups of the fluorescent atomic group pair B having emission intensity and a wavelength(s) that are suitable for detection are selected, and considering the excitation peak wavelength(s) of the fluorescent atomic groups of the fluorescent atomic group pair B, fluorescent atomic groups of the fluorescent atomic group pair A can be selected. The relationship between the emission peak wavelength(s) of the fluorescent atomic groups of the fluorescent atomic group pair A and the excitation peak wavelength(s) of the fluorescent atomic groups of the fluorescent atomic group pair B can be determined considering the FRET effect obtained between them. The two fluorescent atomic groups in the fluorescent atomic group pair A may be identical to or different from each other, and the two fluorescent atomic groups in the fluorescent atomic group pair B may also be identical to or different from each other. When the two fluorescent atomic groups in the fluorescent atomic group pair A or the two fluorescent atomic groups in the fluorescent atomic group pair B are different from each other, the emission peak wavelength of at least one of the two fluorescent atomic groups of the fluorescent atomic group pair A is shorter than the excitation peak wavelength of at least one of the two fluorescent atomic groups of the fluorescent atomic group pair B. It is preferred that the emission peak wavelengths of both of the fluorescent atomic groups of the fluorescent atomic group pair A are shorter than the excitation peak wavelengths of both of fluorescent atomic groups of the fluorescent atomic group pair B.

Characteristic (b)

The fluorescent atomic group pairs A and B exhibit the FRET effect. The Förster resonance energy transfer (FRET) effect is also called Fluorescence resonance energy transfer and is a phenomenon where the excitation energy between adjacent two chromophores is not converted into an electromagnetic wave and is directly transferred by the resonance of electrons. The energy is transferred, by energy of light absorbed by one of the chromophores (donor), to the other chromophore (receptor), and when the receptor is a fluorescent molecule, fluorescence is emitted from the receptor. In the labeled single-stranded nucleic acid of the present invention, the fluorescent atomic group pair A having an emission peak wavelength that is shorter than the excitation peak wavelength of the fluorescent atomic group pair B is arranged so as to exhibit the FRET effect with the fluorescent atomic group pair B. The arrangement by which the fluorescent atomic group pairs A and B exhibit the FRET effect is, for example, an arrangement in the case where a base having the fluorescent atomic group pair A and a base having the fluorescent atomic group pair B are contained in the labeled single-stranded nucleic acid at a distance at which the fluorescent atomic group pairs A and B have the FRET effect. The distance (base length) at which the fluorescent atomic group pairs A and B have the FRET effect is, although it differs according to the types and combinations of fluorescent atomic groups of the fluorescent atomic group pairs A and B, for example, 1 to 11 bases, preferably 2 to 8 bases, more preferably 2 to 7 bases, yet more preferably 2 to 6 bases, yet more preferably 2 to 5 bases, yet more preferably 2 to 4 bases. The distance of one base means that one nucleic acid having no fluorescent atomic group is present between the fluorescent atomic group pairs A and B. Examples of the combinations of the fluorescent atomic groups of the fluorescent atomic group pairs A and B include a combination of thiazole orange (D514) and thiazole pink (D570) or D640 and a combination of D436 and thiazole orange (D514), thiazole pink (D570), or D640.

In addition to the characteristics (a) and (b), the labeled single-stranded nucleic acid of the present invention is optionally characterized in that the fluorescent atomic group pairs A and B are positioned at any of the bases that is at least two bases inward from each end of the labeled single-stranded nucleic acid. By satisfying this characteristic, both of the exciton effect and the FRET effect can be exhibited.

As examples of the base having the fluorescent atomic group pair that exhibits an exciton effect, those described in Patent Literatures 1 and 2 and Non-Patent Literatures 2 to 5 can be shown. The base is described in further detail below.

The base having the fluorescent atomic group pair that exhibits an exciton effect can have a structure represented by the following formula (16), (16b), (17), or (17b):

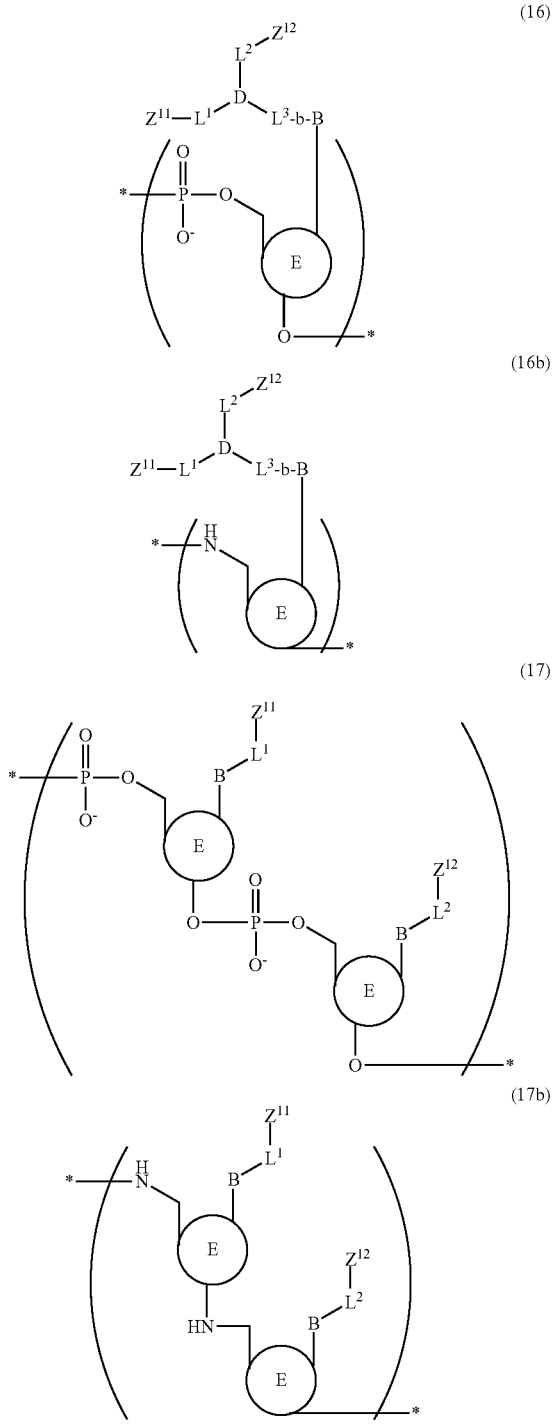

In the formulae (16), (16b), (17), and (17b),

B is an atomic group having a natural nucleobase (adenine, guanine, cytosine, thymine, or uracil) skeleton or an artificial nucleobase skeleton, E is:
(i) an atomic group having a deoxyribose skeleton, a ribose skeleton, or a structure derived from either one of them, or
(ii) an atomic group having a peptide structure or a peptoid structure, $Z^{11}$ and $Z^{12}$ are each a fluorescent atomic group that exhibits an exciton effect, and may be identical to or different from each other, $L^1$, $L^2$, and $L^3$ are each a linker (a linking atom or a linking atomic group), have each any main chain length (the number of main chain atoms), each may or may not contain each of C, N, O, S, P, and Si in the main chain, each may or may not contain each of a single bond, a double bond, a triple bond, an amide bond, an ester bond, a disulfide bond, an imino group, an ether bond, a thioether bond, and a thioester bond in the main chain, and may be identical to or different from each other, D is CR, N, P, P=O, B, or SiR where R is a hydrogen atom, an alkyl group, or any substituent, and b is a single bond, a double bond, or a triple bond, or alternatively, in the formulae (16) and (16b), $L^1$ and $L^2$ are each a linker, $L^3$, D, and b may not be present, and $L^1$ and $L^2$ may be bound directly to B, provided that:

in the formulae (16) and (17), E is an atomic group described in the item (i), and at least one O atom in a phosphoric acid linkage may be substituted with an S atom;

in the formulae (16b) and (17b), E is an atomic group described in the item (ii); and in the formulae (17) and (17b), the respective Bs may be identical to or different from each other, and the respective Es may be identical to or different from each other.

In the formulae (16), (17), (16b), and (17b), the main chain length (the number of main chain atoms) of each of $L^1$, $L^2$, and $L^3$ is preferably an integer of 2 or more. The upper limit of the main chain length (the number of main chain atoms) of each of $L^1$, $L^2$, and $L^3$ is not limited to particular lengths and is, for example, 100 or less, more preferably 30 or less, and particularly preferably 10 or less.

It is preferred that the structure represented by the formula (16) is a structure represented by the following formula (16-1) or (16-2), the structure represented by the formula (16b) is a structure represented by the following formula (16b-1) or (16b-2), the structure represented by the formula (17) is a structure represented by the following formula (17-1), and the structure represented by the formula (17b) is a structure represented by the following formula (17b-1),

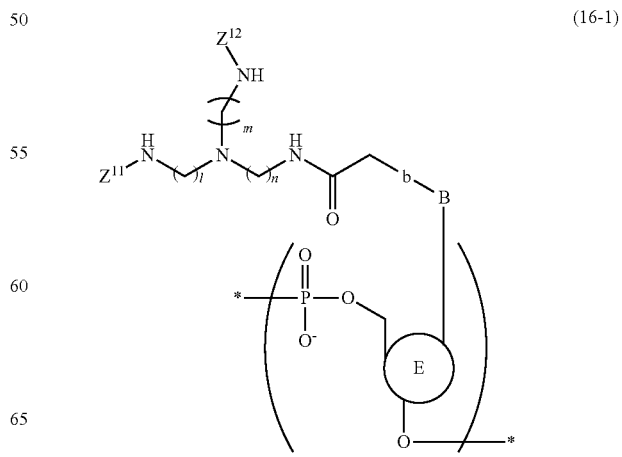

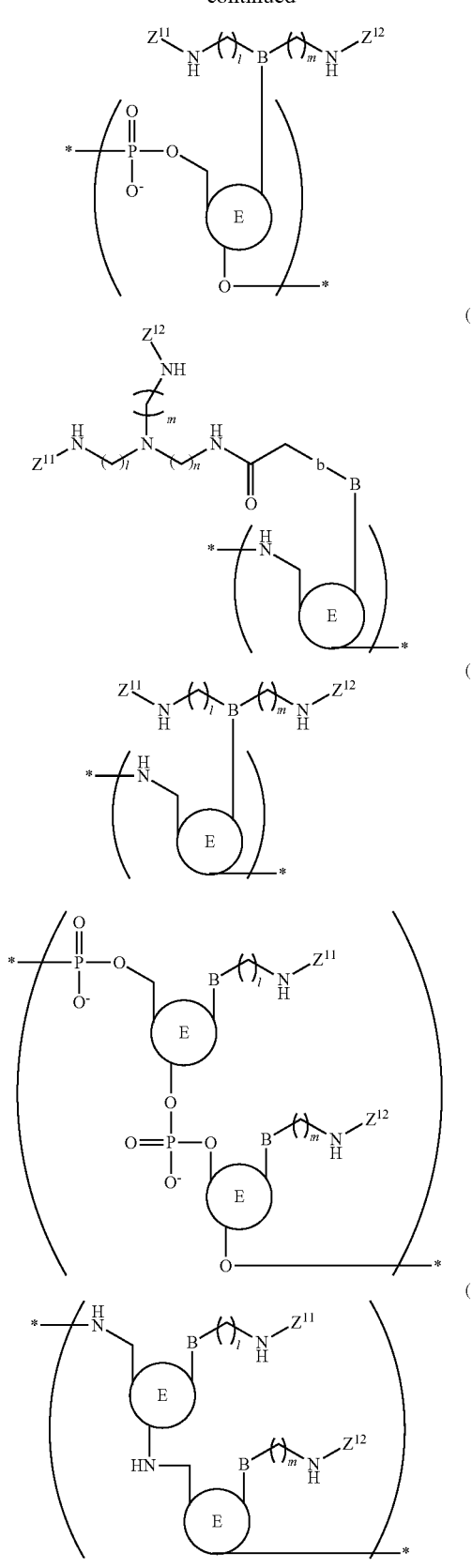

In the formulae (16-1), (16-2), (16b-1), (16b-2), (17-1), and (17b-1), l, m and n are any positive integers, may be identical to or different from each other, each may or may not contain each of C, N, O, S, P, and Si in a main chain thereof, and each may or may not contain each of a single bond, a double bond, a triple bond, an amide bond, an ester bond, a disulfide bond, an imino group, an ether bond, a thioether bond, and a thioester bond in the main chain, B, E, $Z^{11}$, $Z^{12}$, and b are identical to those in the formulae (16), (16b), (17), and (17b), and in the formulae (16-1), (16-2), and (17-1), at least one O atom in a phosphoric acid linkage may be substituted with an S atom.

$Z^{11}$ and $Z^{12}$ are each a fluorescent atomic group that exhibits an exciton effect. Accordingly, for example, an increase in fluorescence at the time of forming a double helix structure is large, and the double helix structure can be further effectively detected.

$Z^{11}$ and $Z^{12}$ are each only required to be a fluorescent atomic group that exhibits an exciton effect, and the fluorescent atomic group is not limited to particular fluorescent atomic groups. In order to exhibit an exciton effect, an aromatic atomic group is preferably used as the fluorescent atomic group. $Z^{11}$ and $Z^{12}$ are each independently, for example, more preferably any of thiazole orange, thiazole pink, oxazole yellow, cyanine, hemicyanine, other cyanine dyes, methyl red, an azo dye, and groups derived therefrom. Any of the dye groups derived from the other known dyes can also be used as appropriate. Many fluorescent dyes that change fluorescence intensity by binding to a nucleic acid such as DNA have been reported. As a typical example, ethidium bromide is known to exhibit intense fluorescence by intercalating with a double helix structure of DNA and is used for DNA detection a lot. Furthermore, fluorescent dyes that can control fluorescence intensity according to the microscopic polarity, such as pyrene carboxamido and prodan are known. Moreover, the thiazole orange is a fluorescent dye in which a benzothiazole ring and a quinoline ring are linked to each other via a methine group and commonly exhibits weak fluorescence and however provides intense fluorescence emission by intercalating with DNA having a double helix structure. In addition to these, examples of $Z^{11}$ and $Z^{12}$ include dyes such as fluorescein and Cy3.

$Z^{11}$ and $Z^{12}$ are each independently preferably an atomic group represented by any of the following formulae (7) to (10):

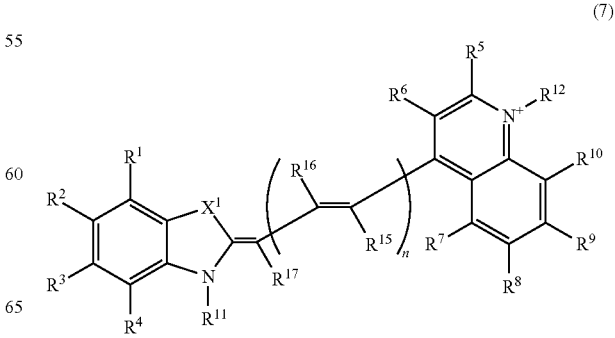

(7)

-continued

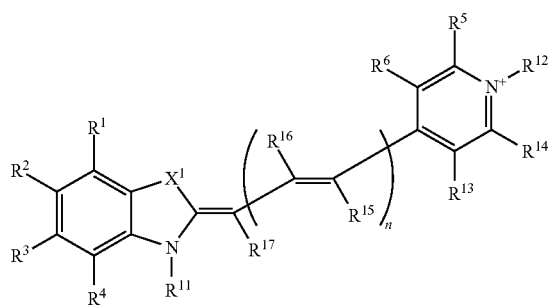
(8)

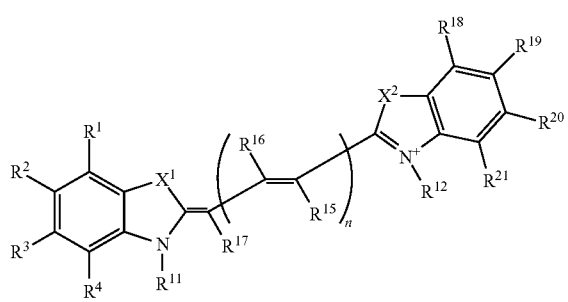
(9)

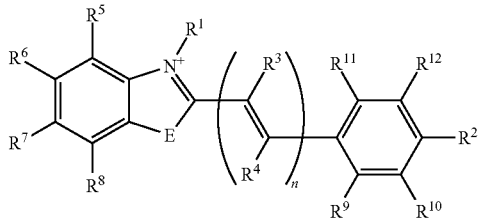
(10)

In the formulae (7) to (9),
X$^1$ and X$^2$ are S or O
n is 0 or a positive integer,
R$^1$ to R$^{10}$ and R$^{13}$ to R$^{21}$ are each independently a hydrogen atom, a halogen atom, a lower alkyl group, a lower alkoxy group, a nitro group, or an amino group,
one of R$^{11}$ and R$^{12}$ is a linking group to be bound to L$^1$ or L$^2$ in the formulae (16), (17), (16b), and (17b), and the other is a hydrogen atom or a lower alkyl group,
when a plurality of R$^{15}$s are present in the formula (7), (8), or (9), they may be identical to or different from each other,
when a plurality of R$^{16}$s are present in the formula (7), (8), or (9), they may be identical to or different from each other, and
X$^1$, X$^2$, and R$^1$ to R$^{21}$ in Z$^{11}$ and X$^1$, X$^2$, and R$^1$ to R$^{21}$ in Z$^{12}$ may be identical to or different from each other, respectively.

In the formula (10),
E is S or O,
R$^2$ to R$^{12}$ are each independently a hydrogen atom, a halogen atom, a lower alkyl group, a lower alkoxy group, a nitro group, or an amino group,
R$^1$ is a linking group to be bound to L$^1$ or L$^2$ in the formulae (16), (17), (16b), and (17b),
when a plurality of R$^3$s is present in the formula (10), they may be identical to or different from each other, and
when a plurality of R$^4$s is present in the formula (10), they may be identical to or different from each other.

In R$^1$ to R$^{21}$ of the formulae (7) to (9), it is more preferred that the lower alkyl group is a straight-chain or branched alkyl group with a carbon number from 1 to 6, and the lower alkoxy group is a straight-chain or branched alkoxy group with a carbon number from 1 to 6. In R$^2$ to R$^{12}$ of the formula (10), it is more preferred that the lower alkyl group is a straight-chain or branched alkyl group with a carbon number from 1 to 6, and the lower alkoxy group is a straight-chain or branched alkoxy group with a carbon number from 1 to 6.

In R$^{11}$ and R$^{12}$ of the formulae (7) to (9) and R$^1$ in the formula (10), it is more preferred that the linking group is a polymethylene carbonyl group with a carbon number of 2 or more and is bound to L$^1$ or L$^2$ in the formulae (16), (16b), (17), and (17b) via a carbonyl group moiety. The upper limit of the carbon number of the polymethylene carbonyl group is not limited to particular numbers and is, for example, 100 or less, preferably 50 or less, more preferably 30 or less, particularly preferably 10 or less.

When Z$^{11}$ and Z$^{12}$ are each represented by any one of the formulae (7) to (9), it is more preferable that they are, for example, each independently a group represented by the formula (19) or (20):

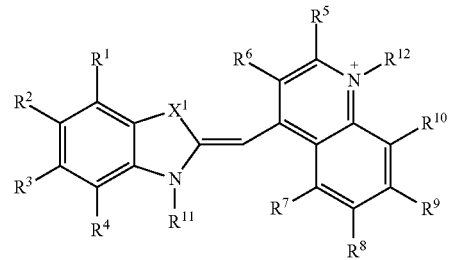
(19)

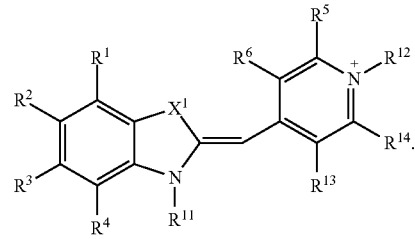
(20)

In the formulae (19) and (20), X$^1$ represents —S— or —O—. R$^1$ to R$^{10}$ and R$^{13}$ and R$^{14}$ each independently indicates a hydrogen atom, a halogen atom, a lower alkyl group, a lower alkoxy group, a nitro group, or an amino group. One of R$^{11}$ and R$^{12}$ is a linking group that is bound to L$^1$ or L$^2$ in the formulae (16), (17), (16b), and (17b), and the other is a hydrogen atom or a lower alkyl group.

Preferred aspects are as follows.
(i) Z$^{11}$ and Z$^{12}$ are each independently an atomic group represented by the formula (19), where X$^1$ is S; R$^1$ to R$^{10}$ are each a hydrogen atom; and either one of R$^{11}$ and R$^{12}$ is a linking group to be bound to L$^1$ or L$^2$ in the formulae (16), (17), (16b), and (17b), and the other is a methyl group.
(ii) Z$^{11}$ and Z$^{12}$ are each independently an atomic group represented by the formula (19), where X$^1$ is S; R$^1$, R$^4$, R$^5$, R$^6$, R$^7$, R$^9$ and R$^{10}$ are each a hydrogen atom; R$^2$, R$^3$, and R$^{12}$ are each a methyl group; R$^8$ is a halogen atom; R$^{11}$ is a linking group to be bound to L$^1$ or L$^2$ in the formulae (16), (17), (16b), and (17b).
(iii) Z$^{11}$ and Z$^{12}$ are each independently an atomic group represented by the formula (7), where X$^1$ is S; n is 1; R$^1$ to $R^{10}$, $R^{15}$, $R^{16}$, and $R^{17}$ are each a hydrogen atom; $R^{11}$ is a linking group to be bound to $L^1$ or $L^2$ in the formulae (16), (17), (16b), and (17b).

$Z^{11}$ and $Z^{12}$ each independently can be an atomic group represented by any one of the following chemical formulae. These formulae represent thiazole orange (D514), D640, D436, D534, D543, and thiazole pink (D570) from the top. Please see Non-Patent Literature 3 for the names of the atomic group that start with D,

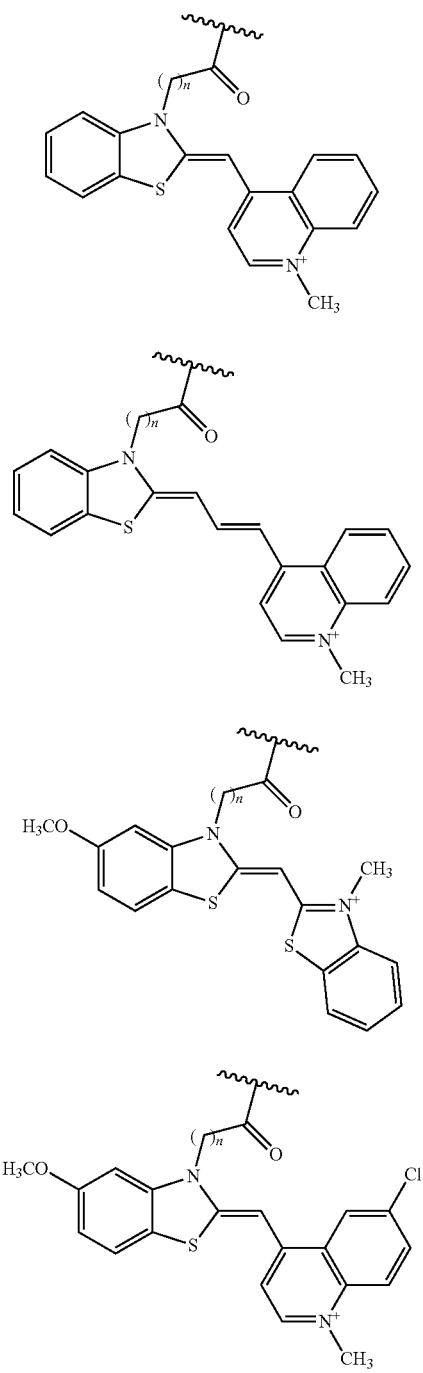

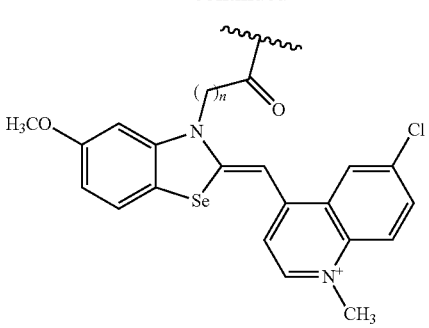

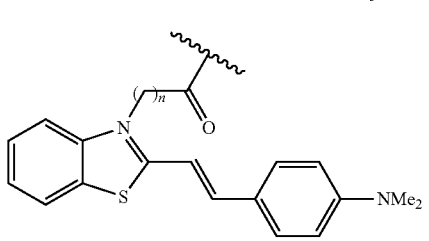

In each of the chemical formulae, n is a positive integer.

In the formulae (16), (17), (16b), and (17b), B may have a natural nucleobase skeleton, and also, as described above, may have an artificial nucleobase skeleton. For example, B preferably is a structure represented by Py (pyrimidine ring), Py der., Pu (purine ring), or Pu der. The Py is an atomic group having a covalent bond to E in the 1-position and a covalent bond to a linker moiety in the 5-position in a six-membered ring represented by the following formula (11). The Py der. is an atomic group in which at least one of all the atoms of the six-membered ring of the Py has been substituted with an N, C, S, or O atom, and the N, C, S, or O atom optionally may have an electric charge, a hydrogen atom, or a substituent. The Pu is an atomic group having a covalent bond to E in the 9-position and a covalent bond to a linker moiety in the 8-position in a condensed ring represented by the following formula (12). The Pu der. is an atomic group in which at least one of all the atoms of a five-membered ring of the Pu has been substituted with an N, C, S, or O atom, and the N, C, S, or O atom optionally may have an electric charge, a hydrogen atom, or a substituent.

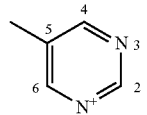

(11)

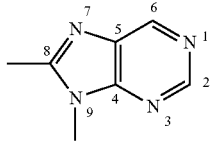

(12)

In the labeled single-stranded nucleic acid of the present invention, the basic skeleton of nucleic acid is not limited to particular basic skeletons. Examples thereof include oligonucleotides, modified oligonucleotides, oligonucleosides, modified oligonucleosides, polynucleotides, modified polynucleotides, polynucleosides, modified polynucleosides, DNAs, modified DNAs, RNAs, modified RNAs, LNAs, PNAs (peptide nucleic acids), chimeric molecules thereof, and other structures. Furthermore, the basic skeleton of each nucleic acid may be a natural one or an artificially synthesized one. In the case of where the present invention is a probe or a primer set, the nucleic acid is not limited to particular nucleic acids as long as it can provide base pairing, for example. In the case of a nucleic acid sample or a target nucleic acid sequence, the nucleic acid is not limited to particular nucleic acids as long as, for example, it serves as a template for synthesizing a complementary strand. Therefore the nucleic acid may be a nucleotide derivative, a part or the whole of which is formed of a completely artificial structure, for example. Artificial bases that compose the nucleic acid can be selected from, for example, 2-amino-6-(N,N-dimethylamino)purine pyridin-2-one, 5-methylpyridin-2-one, 2-amino-6-(2-thienyl)purine, pyrrole-2-carbaldehyde, 9-methylimidazo[(4,5)-b]pyridine, 5-iodo-2-oxo(1H)pyridine 2-oxo-(1H)pyridine, 2-amino-6-(2-thiazolyl)purine, 7-(2-thienyl)-imidazo[4,5-b]pyridine, bromothymine, azaadenine, and azaguanine.

The basic skeleton of the labeled single-stranded nucleic acid of the present invention preferably is an oligonucleotide, a polynucleotide, a DNA, or a modified product thereof. In the present invention, the "nucleotide" may be either deoxynucleotide or ribonucleotide, for example, and the "oligonucleotide" and "polynucleotide" each may be composed of either one of deoxynucleotide and ribonucleotide or may contain both of them. In the present invention, the number of bases that compose the nucleic acid is not limited to particular numbers. Generally, the term "nucleic acid" is synonymous with the term "polynucleotide". Generally, the term "oligonucleotide" is used as a term indicating a polynucleotide composed of a particularly small number of bases, among polynucleotides. In general, a polynucleotide of, for example, 2- to 100-mer, more generally about 2- to 50-mer is referred to as "oligonucleotide", but it is not limited by these numerical values. In the present invention, the term "polynucleotide" also should be interpreted to encompass, for example, polynucleotide and oligonucleotide, as well as artificially synthesized nucleic acids such as peptide nucleic acid, morpholine nucleic acid, methylphosphonate nucleic acid, and S-oligonucleotide acid.

Generally, the peptide nucleic acid (PNA) has a structure in which a deoxyribose main chain of oligonucleotide has been substituted with a peptide main chain. Examples of the peptide main chain include a repeating unit of N-(2-aminoethyl)glycine bound by an amide bond. Examples of the base to be bound to the peptide main chain of PNA include, but not limited to: naturally-occurring bases such as thymine, cytosine, adenine, guanine, inosine, uracil, 5-methylcytosine, thiouracil, and 2,6-diaminopurine; and artificial bases such as bromothymine, azaadenine, and azaguanine.

Generally, LNA is a nucleic acid having two cyclic structures in which, in a sugar-phosphoric acid skeleton, an oxygen atom in the 2'-position and a carbon atom in the 4'-position of ribose are bound to each other by methylene linking. When oligonucleotide containing LNA anneals to DNA, the double-stranded conformation is changed, whereby the thermal stability is improved. LNA has a stronger binding affinity to a nucleic acid than common oligonucleotide. Thus, for example, depending on the conditions for designing the oligonucleotide, more reliable and stronger hybridization can be achieved.

The labeled single-stranded nucleic acid of the present invention includes a labeled structure having at least two fluorescent atomic group pairs. With this configuration, the labeled single-stranded nucleic acid of the present invention has higher specificity to a target and hybridizes to the target more strongly, as compared with an unlabeled nucleic acid that does not include the fluorescent atomic groups, for example. That is, the labeled single-stranded nucleic acid of the present invention has a higher melting temperature (Tm value) than an unlabeled nucleic acid that has a basic skeleton having the same base sequence and the same nucleic acid fragment length. Thus, the labeled single-stranded nucleic acid of the present invention can hybridize to a target more strongly as compared with the unlabeled nucleic acid. Accordingly, the labeled single-stranded nucleic acid of the present invention having such properties allows detection to be carried out efficiently with high specificity, for example.

Because the labeled single-stranded nucleic acid of the present invention also has the above-described characteristics, it can be applied as technology to improve the specificity of amplification by increasing the Tm value, similarly to, for example, conventional PNA or LNA. Furthermore, when PNA or LNA is employed for the basic skeleton of the labeled primer of the present invention, the Tm value can be increased further as compared with unlabeled PNA or LAN, so that the hybridization efficiency can be improved still further. In particular, when mutations of one to several bases are to be discriminated or when insertion or deletion is to be detected as described below, the use of the labeled single-stranded nucleic acid (including, for example, labeled PNA and labeled LNA) of the present invention allows detection to be carried out efficiently with high specificity. When the labeled single-stranded nucleic acid of the present invention is used as a primer or a probe, a large difference in Tm value and a difference in hybridization efficiency are obtained between the cases where it fully matches or mismatches with a target sequence. Accordingly, mutation detection such as single base discrimination can be carried out more easily. Moreover, since the labeled single-stranded nucleic acid of the present invention has a higher Tm value than the unlabeled nucleic acid, it also is applicable as a primer to, for example, a PCR clamp method, a PNA PCR clamp method, an LNA PCR clamp method, and a PNA-LNA PCR clamp method, in which it binds to a specific region strongly, masks the region, and does not serve as a template for amplification.

Specific examples of the structure represented by the formula (16) include nucleotide structures represented by the following formulae (1-3) to (1-10), geometric isomers and stereoisomers thereof, or salts thereof, (1-3)
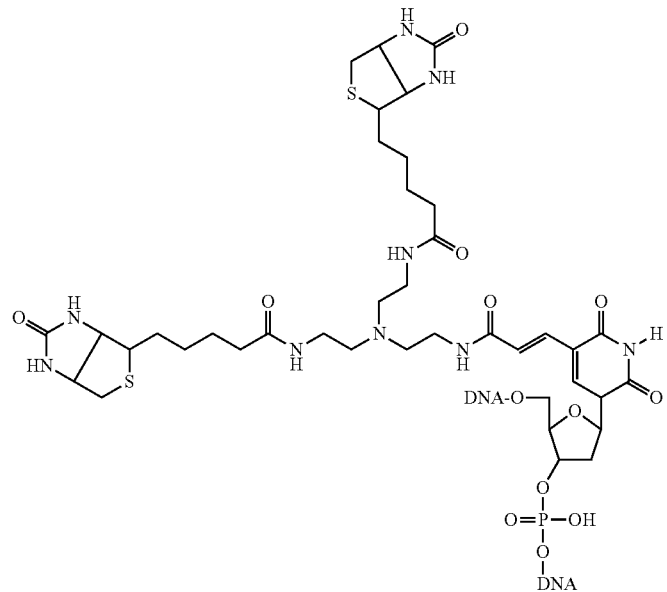
106
(1-4)
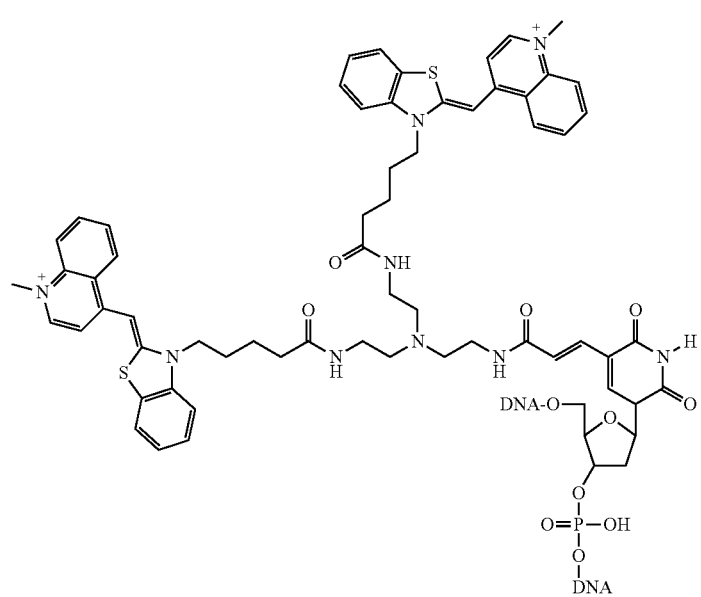
110

(1-5)
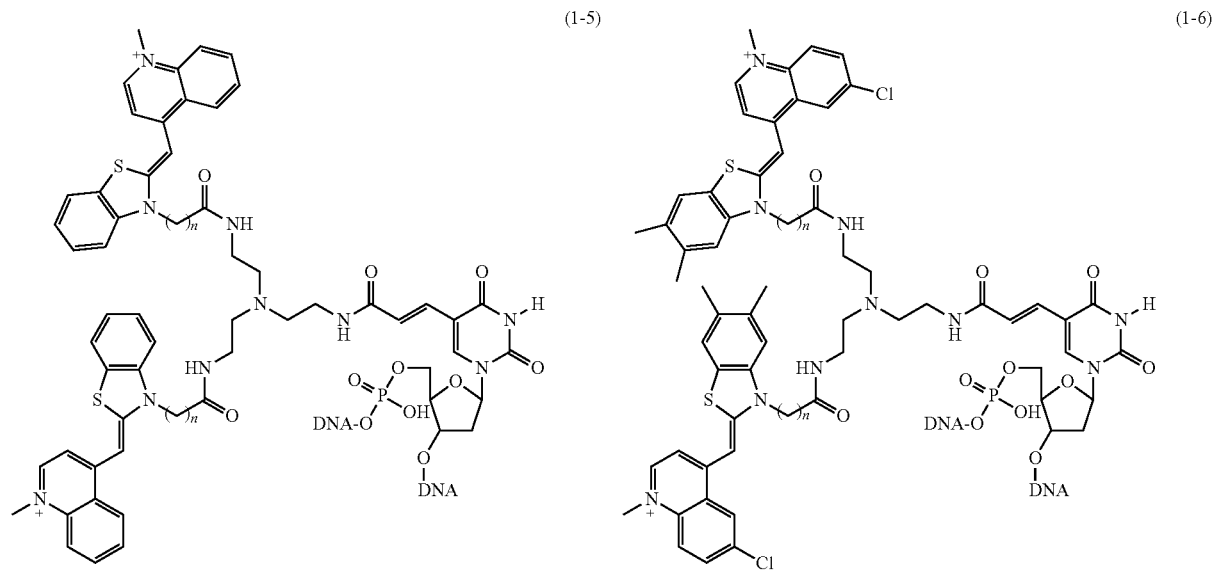
(1-6)
(1-7)
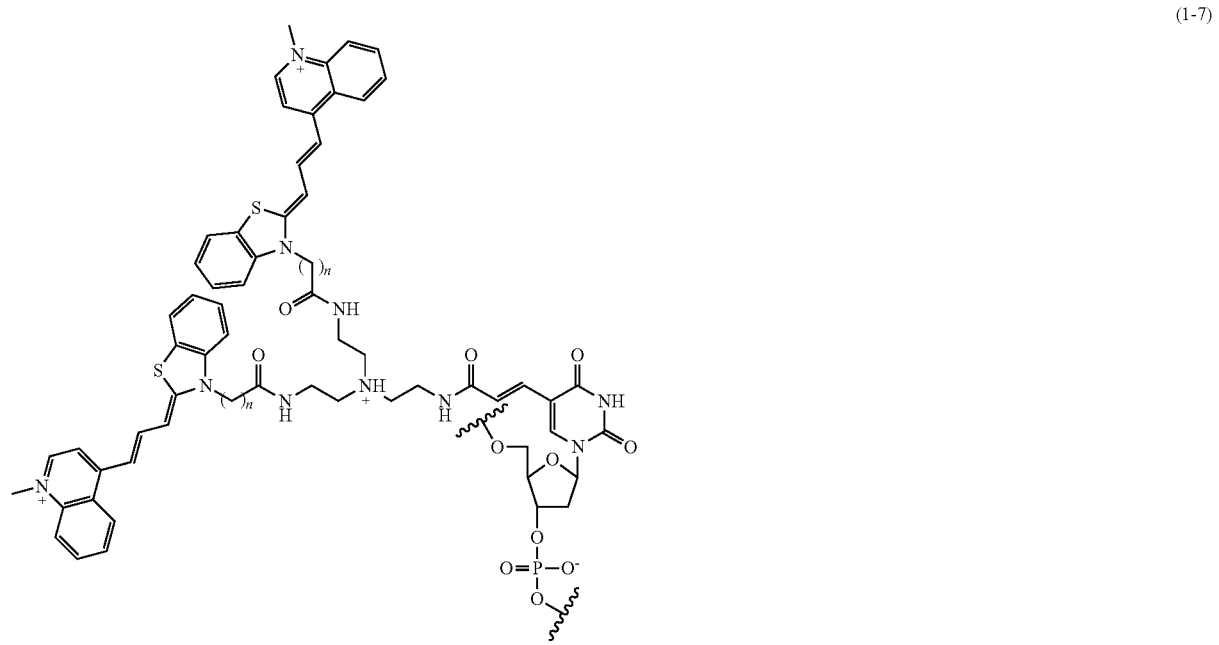

-continued (1-8)

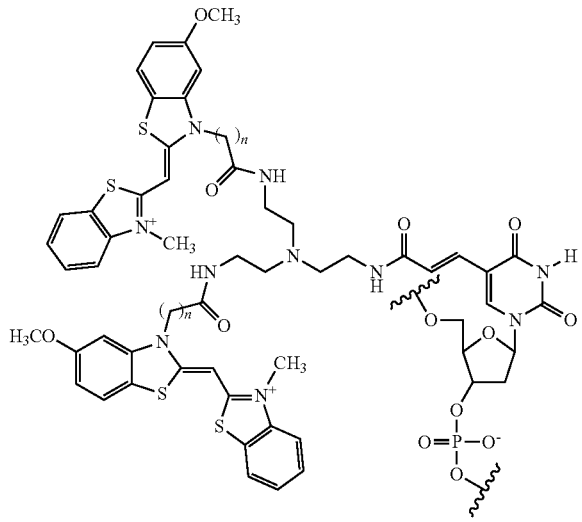

(1-9)

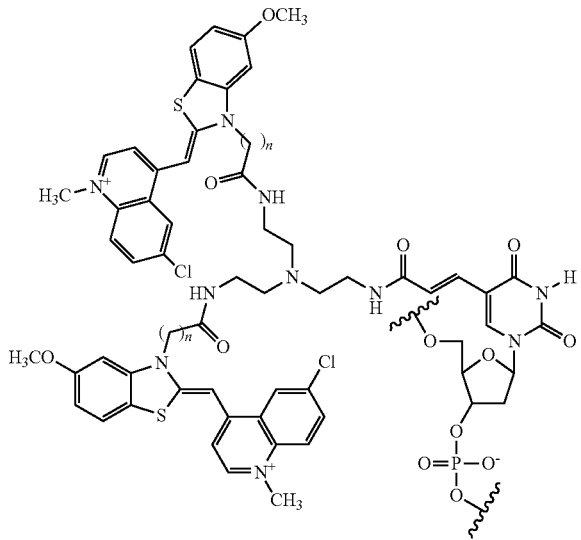

(1-10)

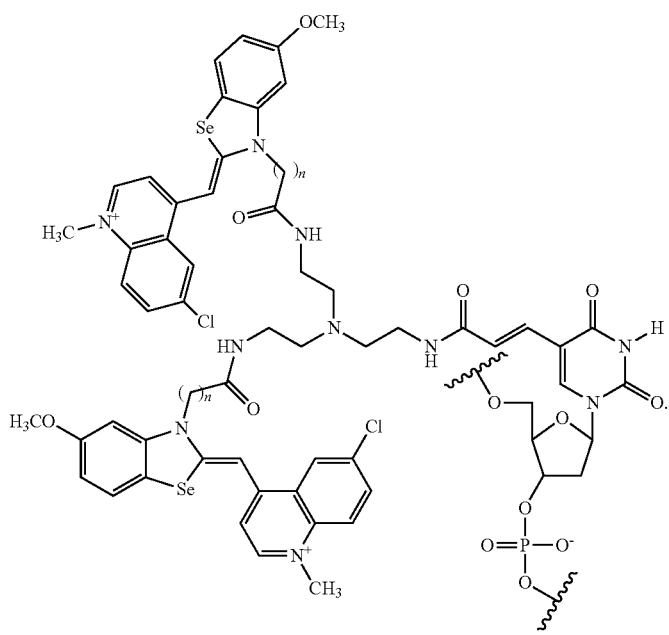

In the formulae (1-3) to (1-10), n is a positive integer.

The labeled single-stranded nucleic acid of the present invention is particularly preferably a labeled single-stranded nucleic acid having fluorescent atomic group pairs represented by the above-mentioned formulae (1-1) to (1-10).

Each one of the fluorescent atomic group pairs in the labeled single-stranded nucleic acid of the present invention is characterized in that:

(i) the one that emits fluorescence, with two planar chemical structures contained in one molecule, which exist not in the same plane but with a certain angle formed therebetween, being located so as to be arranged in the same plane when the molecule undergoes intercalation into or groove binding to a nucleic acid, (ii) the one formed of at least two dye molecule groups that do not exhibit fluorescence emission due to the exciton effect obtained when at least two dye molecules aggregate in parallel to each other but exhibit fluorescence emission with the aggregation state being resolved when the molecules undergo intercalation into or groove binding to a nucleic acid, or (iii) the one having a chemical structure of at least two dye molecules contained in one molecule, with the at least two dye molecules not exhibiting fluorescence emission due to the exciton effect obtained when they aggregate in parallel to each other but exhibiting fluorescence emission with the aggregation state being resolved when the molecules undergo intercalation into or groove binding to a nucleic acid.

In the case of (ii) or (iii), it is preferable that the dye molecule be the molecule described in (i).

[Synthesis of Labeled Single-Stranded Nucleic Acid]

The labeled single-stranded nucleic acid of the present invention can be prepared with reference to the methods described in Patent Literatures 1 and 2. For example, the compounds represented by the formulae (1-1) to (1-10) can also be synthesized with reference to the methods described in Patent Literatures 1 and 2.

For example, the following production methods (synthesis methods) can be used for the production of the labeled single-stranded nucleic acid of the present invention. That is, as an easy DNA labeling method, a method in which an active amino group contained in DNA and an activated carboxyl group in a labeling agent are reacted with each other in a buffer solution has been used widely. This method can be used particularly for introduction of a linker or a dye. Examples of the method for introducing an amino group include a method using an amino modifier phosphoramidite commercially available from GLEN RESEARCH.

A method for synthesizing a nucleic acid having, as a basic skeleton, a modified DNA is well known. For example, it can be synthesized by a so-called phosphoramidite method. A phosphoramidite reagent to serve as a raw material thereof also can be synthesized easily by a known method. When the nucleic acid of the present invention is DNA, particularly a short oligo-DNA, it can be synthesized easily with an automated DNA synthesizer or the like, for example. Furthermore, it is also possible to synthesize a long-chain nucleic acid (DNA) etc. by, for example, PCR. As described above, the position where DNA and a dye molecule are bound to each other is not limited to particular nucleic acids, and particularly preferably is the 5-position of thymidine, for example. Triphosphoric acid of a nucleotide derivative with various substituents being extended from the 5-position of thymidine is known to have a relatively high efficiency of introduction carried out with DNA polymerase. Accordingly, the nucleic acid of the present invention can be synthesized easily, for example, not only when it is a short oligo-DNA but also when it is a long-chain DNA.

Particularly, a fluorescence primer (labeled nucleic acid) of the present invention, which is a single-stranded DNA, with, for example, thiazole orange used therein has the following advantages, for example: (1) it can be synthesized easily because it can be prepared merely by introducing, in a buffer solution, a dye into DNA synthesized with an automated DNA synthesizer; and (2) it is also possible to produce a long-chain fluorescence primer by reacting a dye with a long-chain DNA prepared enzymatically. Furthermore, it can be excited with light having a relatively long wavelength around, for example, 500 nm.

The labeled single-stranded nucleic acid of the present invention is used as a probe to be hybridized with a target nucleic acid or a primer for amplifying a target nucleic acid.

The present invention encompasses a method for detecting a target nucleic acid, including measuring fluorescence under the conditions where the labeled single-stranded nucleic acid of the present invention as a probe is capable of hybridizing with a target nucleic acid, to determine the presence or absence of the hybridization of the target nucleic acid with the probe. The nucleic acid amplification method that can be used in the method for detecting a target nucleic acid is specifically as follows.

This nucleic acid amplification method is a method for amplifying a target nucleic acid sequence in a nucleic acid sample, including the following steps (A) and (B'):
(A) the step of providing a nucleic acid sample; and
(B') the step of including the following steps (B1') and (B2'):
(B1') the step of amplifying a target nucleic acid sequence in the nucleic acid sample using a primer or a primer set containing a pair of primers; and
(B2') the step of hybridizing a single-stranded nucleic acid sequence amplified in the step (B1') with a probe composed of the labeled single-stranded nucleic acid of the present invention.

The probe composed of the labeled single-stranded nucleic acid of the present invention can contain at least one of the structures represented by the formulae (16), (16b), (17), and (17b), for example.

The primer and the primer set in the nucleic acid amplification method is not limited to particular primers and primer sets and, for example, can be set, as appropriate, according to the target nucleic acid sequence to be amplified, the type of the nucleic acid amplification reaction, and the like. Moreover, the type of the nucleic acid amplification method in the present invention is not limited to particular methods, and examples thereof include various isothermal amplification methods such as the SMAP method and the LAMP method and the PCR method. The nucleic acid amplification can be carried out in the same manner as in the nucleic acid amplification method.

The base sequence of the labeled single-stranded nucleic acid of the present invention used as a probe can be designed, as appropriate, according to the target nucleic acid sequence and is designed in such a manner that the probe hybridizes to the target nucleic acid under a stringent condition. The "stringent condition" can be determined depending on, for example, the melting temperature Tm (° C.) of the double strand formed of the probe of the present invention and a complementary strand thereto, and the salt concentration of the hybridization solution. Specific examples can be found in a reference such as J. Sambrook, E. F. Frisch, T. Maniatis; Molecular Cloning $2^{nd}$ edition, Cold Spring Harbor Laboratory (1989). (The entire disclosure of which is incorporated herein by reference).

In the nucleic acid amplification method, the labeled single-stranded nucleic acid of the present invention is used as a probe. Therefore, for example, the presence or absence of amplification of the target nucleic acid sequence can be determined, for example, by only detecting the fluorescence intensity of a nucleic acid amplification reaction solution. This is, for example, for the following reasons. When a probe is hybridized with a complementary nucleic acid sequence, a double-stranded nucleic acid is formed. A nucleobase skeleton (dye) of the labeled primer is thus intercalated with or groove-bound to the double-stranded nucleic acid. At that time, for example, the above-mentioned exciton effect of the nucleobase skeleton (dye) is not exhibited, and therefore the nucleobase skeleton generates fluorescence emission. On the other hand, when a probe is not hybridized with a complementary nucleic acid sequence, the exciton effect is exhibited, and the nucleobase skeleton thus does not generate fluorescence emission. Therefore, for example, when a probe is not hybridized with an amplification product obtained by a nucleic acid amplification reaction, or amplification does not occur, no nucleobase skeleton that generates fluorescence emission is found or increased. Accordingly, detection of increased fluorescence intensity is determined as amplifying the target nucleic acid sequence, and detection of non-increased fluorescence intensity is determined as amplifying no target nucleic acid sequence. Specifically, the labeled single-stranded nucleic acid of the present invention is advantageous in that the detection sensitivity is high, as compared with the conventional labeled probe having an exciton effect because of the low fluorescent background at the time of no hybridization.

The labeled single-stranded nucleic acid used as a probe may be, for example, added to a reaction solution before or after the nucleic acid amplification reaction in the step (B1'). In the former case, the fluorescence intensity may be detected continuously or discontinuously in parallel with the nucleic acid amplification reaction in the step (B1') or after the completion of the step (B1'). When the detection is carried out after the completion of the step (B1'), it is preferred that the detection is carried out also before the initiation of the reaction in the step (B1') as a background. On the other hand, when the steps (B1') and (B2') are carried out individually, it is, for example, preferred that the labeled single-stranded nucleic acid as a probe is added to a reaction solution after the nucleic acid amplification reaction in the step (B1'), for example. In this case, the fluorescence intensity is detected after the step (B1'), for example. At that time, it is preferred that the fluorescence intensity after the step (B1') and before or immediately after the addition of the labeled single-stranded nucleic acid as a probe is also detected as a background, for example. A specific example of the detection is as mentioned above.

(1) The labeled single-stranded nucleic acid of the present invention as a probe can be used in a homogeneous assay (96-well microplate or capillary) in a liquid phase.

(2) The labeled single-stranded nucleic acid of the present invention as a probe can be used as a PCR probe and can be applied to detection (real-time PCR) of amplification curve obtained during a DNA amplification reaction or a low-cost method as a substitute for a TaqMan probe. It can also be used as a label of primer or an internally labeled probe.

(3) The labeled single-stranded nucleic acid of the present invention as a probe can also be used as a capture probe or a labeled probe in a DNA chip. The method of the present invention is a high-throughput, reagent-free system and requires no labeling process and washing process. Artificial errors can be largely avoided. Simultaneous multi-item (high throughput) analysis can be carried out on glass or a solid phase support material as a substitute for the glass (a base plate such as gold, ITO, or copper and a material such as diamond and plastics, to which many specimens can be attached).

(4) The labeled single-stranded nucleic acid of the present invention as a probe can be immobilized on beads, fibers, or hydrogel. Genes can be detected under the environments of semiliquid or semisolid. The probe can be used under the liquid-like measurement environment and also can be carried as if it is a solid.

(5) The labeled single-stranded nucleic acid of the present invention as a probe can be used as a probe for blotting (Southern blotting, Northern blotting, dot blotting). Only an intended gene fragment can be caused to emit fluorescence and thus can be detected. According to the method of the present invention, washing after the hybridization operation is not required.

(6) The labeled single-stranded nucleic acid of the present invention as a probe can be used as a probe for detecting/tracing an intracellular nucleic acid. Accordingly, intracellular DNA/RNA can be spatiotemporally analyzed. A fluorescence microscope or a cell sorter can be used. The probe can be applied to DNA labeling, transcription into RNA/tracing of splicing, functional analysis of RNAi, and the like. The method of the present invention does not require washing and thus is suitable for tracing the function of living cells.

(7) The labeled single-stranded nucleic acid of the present invention as a probe can be used as a probe for fluorescence in situ hybridization (FISH). By the method of the present invention, tissues can be stained. The method of the present invention does not require washing, and artificial errors are thus small. That is, the labeled single-stranded nucleic acid of the present invention as a probe functions as a fluorescent dye that does not emit fluorescence at the time of not recognizing a target biomolecule. Thus, by using the probe, bioimaging in which a complicated washing step is not required can be established. This leads to real-time fluorescence observation with high reliability and low effort.

(8) In the labeled single-stranded nucleic acid of the present invention as a probe, chromophores with a plurality of wavelengths can be used. Thus, at the time when detection/tracing is carried out at one molecular level, a design of largely avoiding background light and scattering light of excitation light can be easily constructed. For example, at the time of observing a biomolecule at one molecular level, the background light and scatting light of excitation light caused by leakage of the excitation light interfere. Thus, various methods for avoiding this are required. The present invention is particularly useful in this case.

The fluorescence intensity of the labeled single-stranded nucleic acid of the present invention as a probe can be, for example, changed by controlling an exciton interaction of bound dye portion. In the present invention, sufficiently high quenching performance for functioning as an on-off probe can be obtained specifically by an approach using the exciton interaction. Such design of on-off fluorescent nucleotide is really important for, for example, establishing a bioimaging assay that does not require washing. The photophysical properties exerted by the probe using the exciton effect are really characteristic and also favorable for design of a novel fluorescent DNA probe for DNA sequencing (sequence determination), genotyping (genotype analysis), monitoring of DNA conformation transition, and gene expression observation.

When the labeled single-stranded nucleic acid of the present invention is used as a probe, the generation of phenomena such as amplification/decomposition/protein binding of the sequence can be immediately detected, and the amounts of the phenomena can be quantitatively determined by the quantitative determination of the target nucleic acid sequence, for example. This detection and quantitative determination can be carried out as follows, and this, however, is merely an example, and does not limit the present invention. That is, first, a probe (nucleic acid) of the present invention hybridizes to a target nucleic acid sequence at a constant amount-of-substance ratio, thereby forming a double strand. The amount of substance of the formed double strand is directly proportional to the amount of substance of the target nucleic acid sequence. Thus, by measuring the fluorescence intensity of the double stand, the target nucleic acid sequence can be detected, and the amount of substance of the target nucleic acid sequence can be quantitatively determined. In this case, in the labeled single-stranded nucleic acid of the present invention, background fluorescence emission is further suppressed. Thus, the measurement of fluorescence intensity of the double strand is not interfered, and further accurate measurement can be achieved.

The present invention encompasses a method for amplifying a target nucleic acid, including amplifying a target nucleic acid using the labeled single-stranded nucleic acid of the present invention as a primer. As the method for amplifying a target nucleic acid using the labeled single-stranded nucleic acid of the present invention as a primer, conventionally known various nucleic acid amplification methods can be shown as examples, and the reaction system is not at all limited. Examples of the nucleic acid amplification methods include an isothermal amplification method and a polymerase chain reaction (PCR) method. The isothermal amplification method typically is a method in which a nucleic acid amplification reaction is carried out isothermally. Examples of such method include a strand displacement amplification (SDA) method disclosed in JP H07-114718 A (the entire disclosure of which is incorporated herein by reference.); an improved SDA method disclosed in U.S. Pat. No. 5,824,517 (the entire disclosure of which is incorporated herein by reference.), WO 99/09211 (the entire disclosure of which is incorporated herein by reference.) or WO 95/25180 (the entire disclosure of which is incorporated herein by reference.); a nucleic acid sequence based amplification (NASBA) method disclosed in Japanese Patent No. 2650159 (the entire disclosure of which is incorporated herein by reference.); Loop-Mediated Isothermal Amplification (LAMP) method disclosed in WO 00/28082 (the entire disclosure of which is incorporated herein by reference.); an Isothermal and Chimeric primer-initiated Amplification of Nucleic acids (ICAN) method disclosed in WO 02/16639 (the entire disclosure of which is incorporated herein by reference.); a self-sustained sequence replication (3SR) method; a transcription-mediated amplification (TMA) method; a Q beta replicase method disclosed in Japanese Patent No. 2710159 (the entire disclosure of which is incorporated herein by reference.); and methods disclosed in Japanese Patent No. 389726 (the entire disclosure of which is incorporated herein by reference.), Japanese Patent No. 3942627 (the entire disclosure of which is incorporated herein by reference.), and NATURE METHODS (Vol. 4, No. 3, March 2007, pp. 257-262) (the entire disclosure of which is incorporated herein by reference.), Mitani Y., et. al., 2007., Nat. Methods 4(3): 257-262. (the entire disclosure of which is incorporated herein by reference) (hereinafter referred to as SmartAmp (Smart Amplification Process) method), an Invader method, and a rolling cycle amplification (RCA) method.

EXAMPLES

The present invention is described in further detail below with reference to the examples. The present invention, however, is not limited by the following examples.

Example 1

Oligo DNA strands into each of which thiazole orange (TO) and thiazole pink (TP) had been introduced as scaffolds were synthesized by an amidite method described in Patent Literature 2 (for example, see Example 2). TO was introduced by introducing NHS-Carboxy-dT into an intended position and immediately thereafter causing TO2 diamidite to react therewith and then synthesizing a sequence after the position by a conventional method. Cutting out from CPG and deprotection were carried out in 28% ammonia water at 55° C. for 4 hours. Purification was carried out by HPLC equipped with a reverse-phase (RP-18) column.
TO2 Diamide

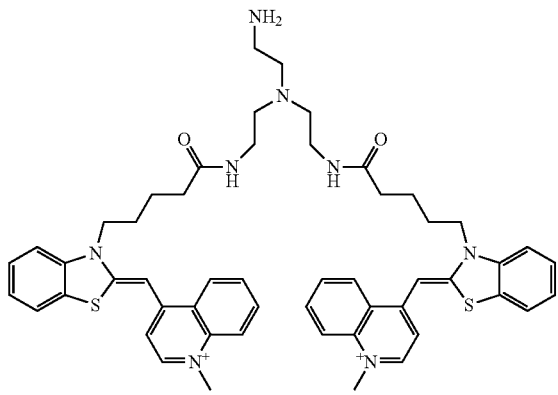 [SMILES: C[n+]1ccc(/C=C2\Sc3ccccc3N2CCCCC(=O)NCCN(CCN)CCNC(=O)CCCCN2/C(=C/c3cc[n+](C)c4ccccc34)Sc3ccccc32)c2ccccc21]

Thereafter, a nucleic acid obtained after the purification and TP-ester were caused to react with each other in a sodium bicarbonate buffer according to the method described in Patent Literature 1 (for example, Example 6 (see (synthesis of compound into which two structures induced from thiazole orange into one molecule had been introduced)), and purification was carried out by HPLC equipped with a reverse-phase (RP-18) column. Thus, an intended product was obtained.
TP-Ester

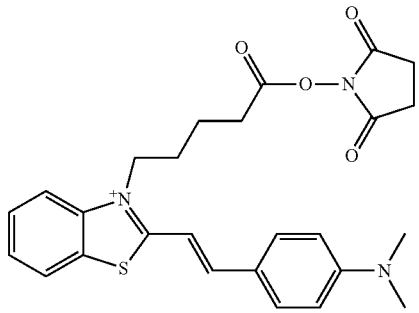 [SMILES: CN(C)c1ccc(/C=C/c2sc3ccccc3[n+]2CCCCC(=O)ON2C(=O)CCC2=O)cc1]

TP-Ester

Oligo DNA strands into each of which thiazole orange (TO) and thiazole pink (TP) had been introduced (SEQ ID NO: 1 (base sequences are common in five strands), prepared by the method are as follows.

```
20-mer.EX16-12TOTP:
5'-TGTGZATCtTTCTCTTTCTC-3'

20-mer.EX8-12TOTP:
5'-TGTGTATCtTTCZCTTTCTC-3'

20-mer.EX10-12TOTP:
5'-TGTGTATCtTZCTCTTTCTC-3'

20-mer.EX14-12TOTP:
5'-TGTGTAZCtTTCTCTTTCTC-3'

20-mer.EX18-12TOTP:
5'-TGZGTATCtTTCTCTTTCTC-3'
```

(Z represents T labeled with TO, and t represents T labeled with TP)

Example 2

(Spectrum Comparison Experiment Between Fluorescence Nucleic Acid Probe into which Two Fluorescent Dyes Having Exciton Effect have been Introduced and Conventional Fluorescence Probe Having Exciton Effect)

Figure 1B:
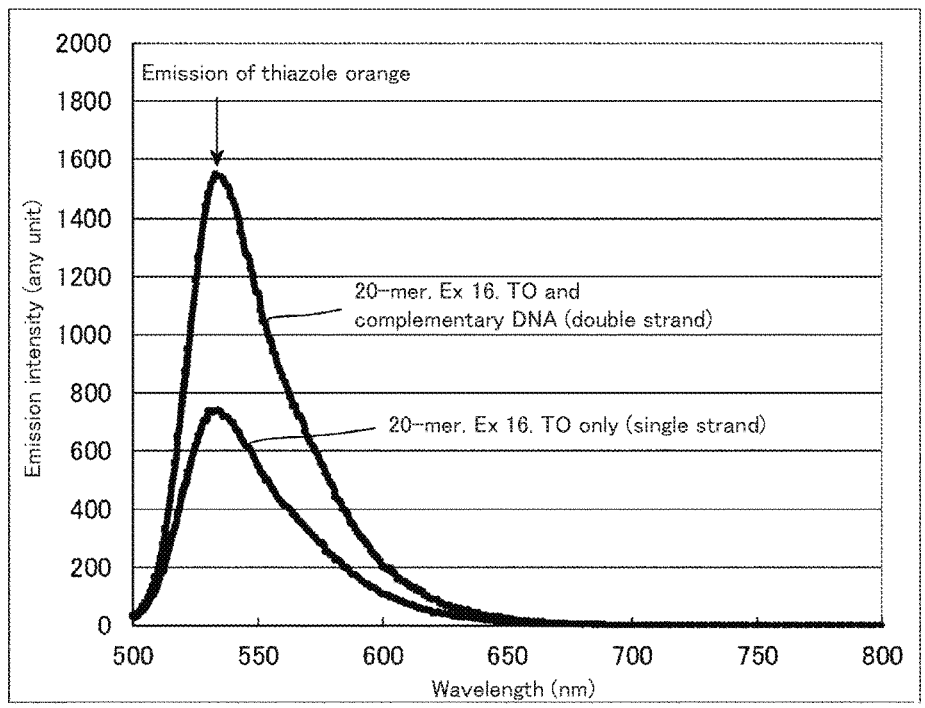
FIG. 1 B shows a result of spectrum measurement of a conventional fluorescent nucleic acid probe (conventional art) into which one fluorescent dye having an exciton effect has been introduced, obtained in Example 1. This result was obtained using oligonucleotide (EX16.TO) having the same sequence as EX16-12TOTP and thiazole orange (TO) at the 16th base from the 3' end.
FIG. 1C shows a result of spectrum measurement of a fluorescent nucleic acid probe (conventional art) into which one fluorescent dye having an exciton effect has been introduced, obtained in Example 1. This result was obtained using oligonucleotide (EX16.TP) having the same sequence as EX16-12TOTP and thiazole orange (TP) at the 12th base from the 3' end.
Figure 1C:
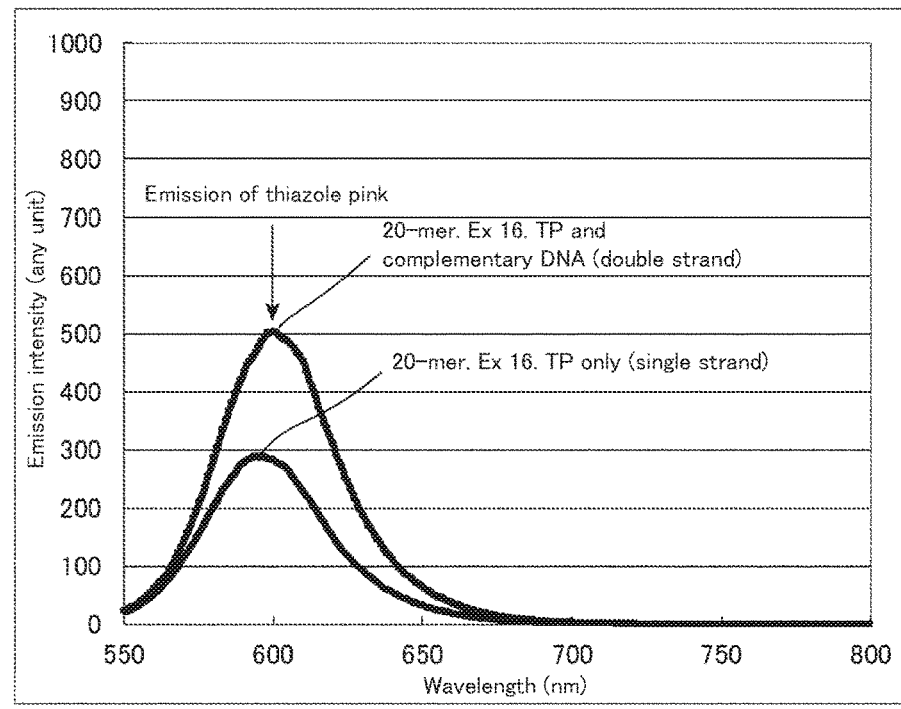
Figure 2A:
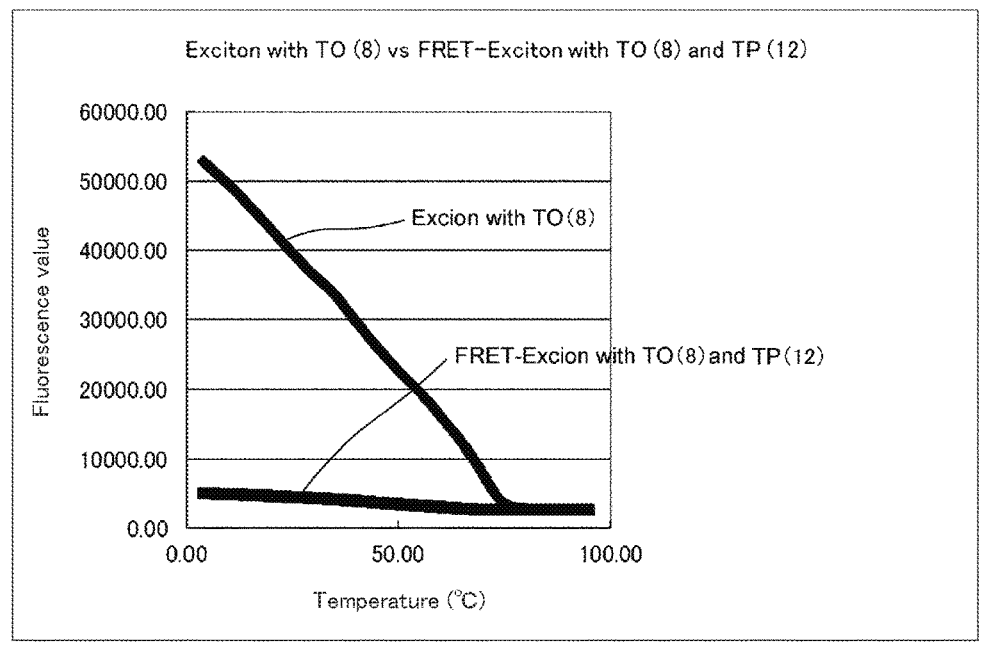
FIG. 2A shows a result of melting curve analysis of a fluorescence nucleic acid probe (EX8-12TOTP) into which two fluorescent dyes having an exciton effect have been introduced, obtained in Example 1 (the distance between thiazole orange (TO, at 8th base from the 3' end) and thiazole pink (TP, at the 12th base from the 3' end): 3 bases). As a comparison, the result of melting curve analysis of a fluorescence nucleic acid probe into which only thiazole orange (TO) has been introduced into the same position is shown.
Figure 2B:
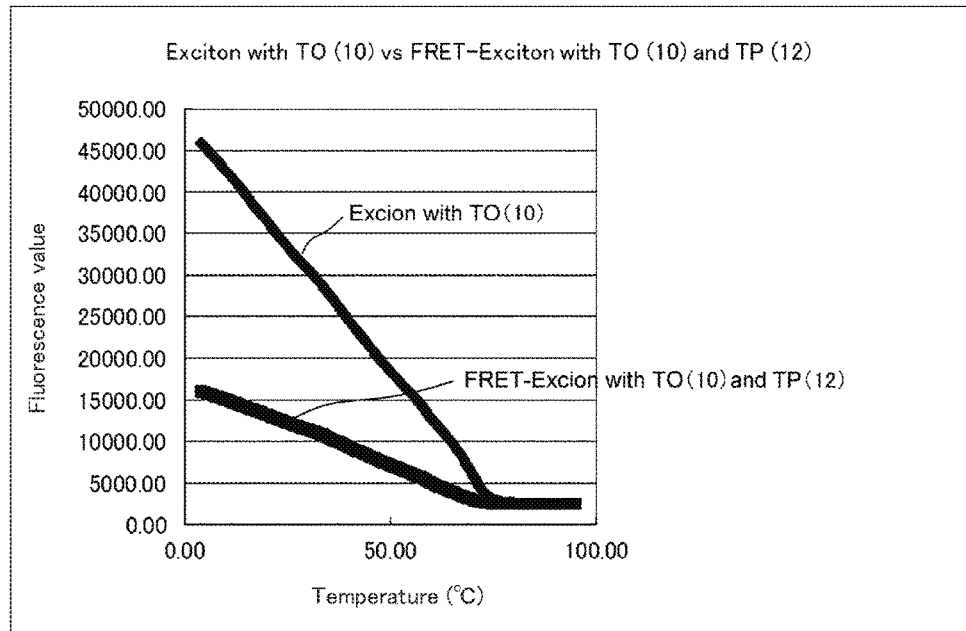
FIG. 2B shows a result of melting curve analysis of a fluorescence nucleic acid probe (EX10-12TOTP) into which two fluorescent dyes having an exciton effect has been introduced, obtained in Example 1 (the distance between thiazole orange (TO, at 10th base from the 3' end) and thiazole pink (TP, at the 12th base from the 3' end): 1 base). As a comparison, the result of melting curve analysis of a fluorescence nucleic acid probe into which only thiazole orange (TO) has been introduced into the same position is shown.
Figure 2C:
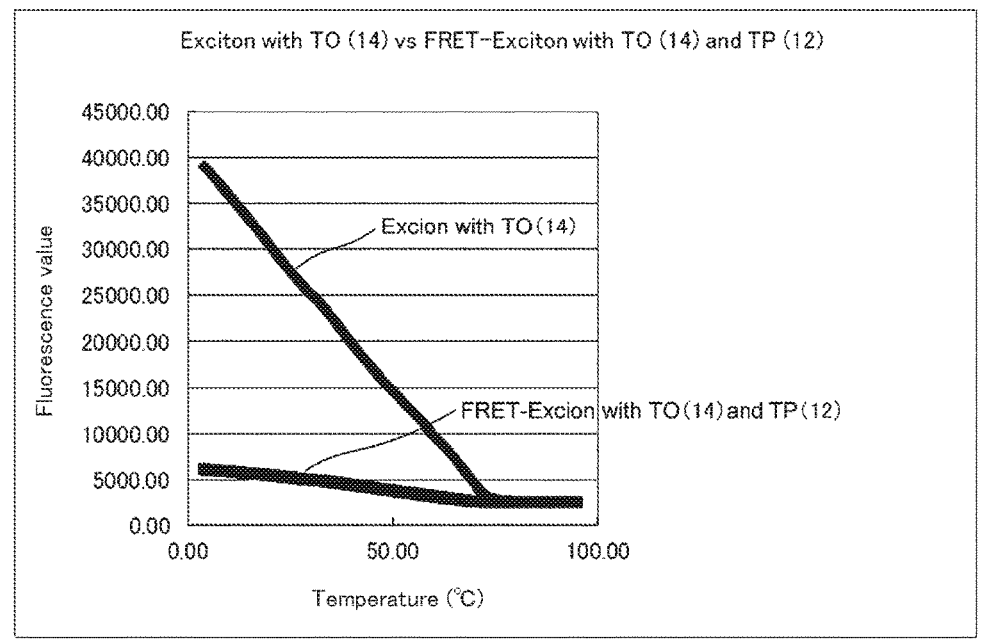
FIG. 2C shows a result of melting curve analysis of a fluorescence nucleic acid probe (EX14-12TOTP) into which two fluorescent dyes having an exciton effect have been introduced, obtained in Example 1 (the distance between thiazole orange (TO, at 14th base from the 3' end) and thiazole pink (TP, at the 12th base from the 3' end): 1 base). As a comparison, the result of melting curve analysis of a fluorescence nucleic acid probe into which only thiazole orange (TO) has been introduced into the same position is shown.
Figure 2D:
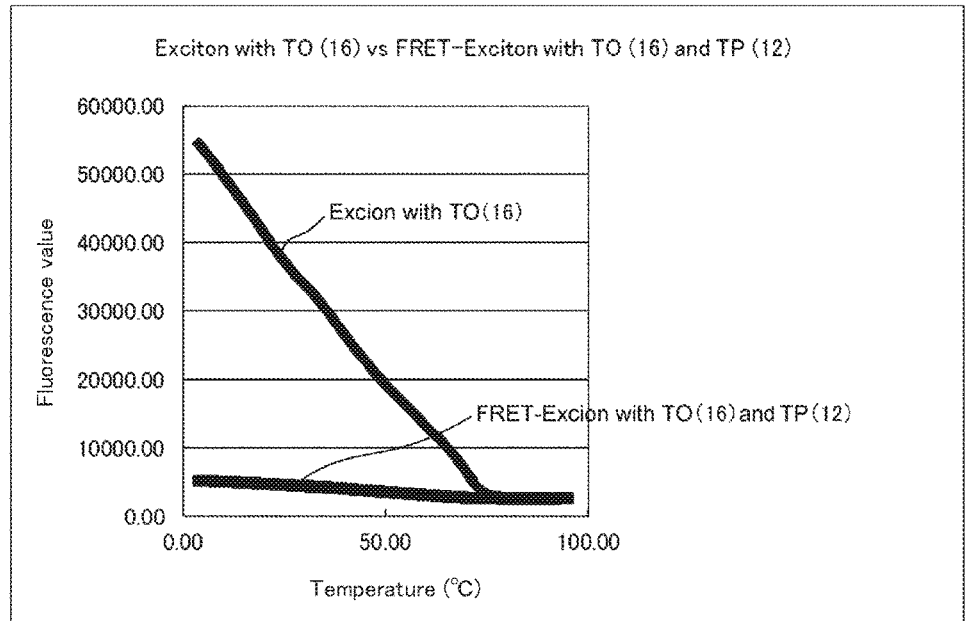
FIG. 2D shows a result of melting curve analysis of a fluorescence nucleic acid probe (EX16-12TOTP) into which two fluorescent dyes having an exciton effect have been introduced, obtained in Example 1 (the distance between thiazole orange (TO, at 16th base from the 3' end) and thiazole pink (TP, at the 12th base from the 3' end): 4 bases). As a comparison, the result of melting curve analysis of a fluorescence nucleic acid probe into which only thiazole orange (TO) has been introduced into the same position is shown.
Figure 2E:
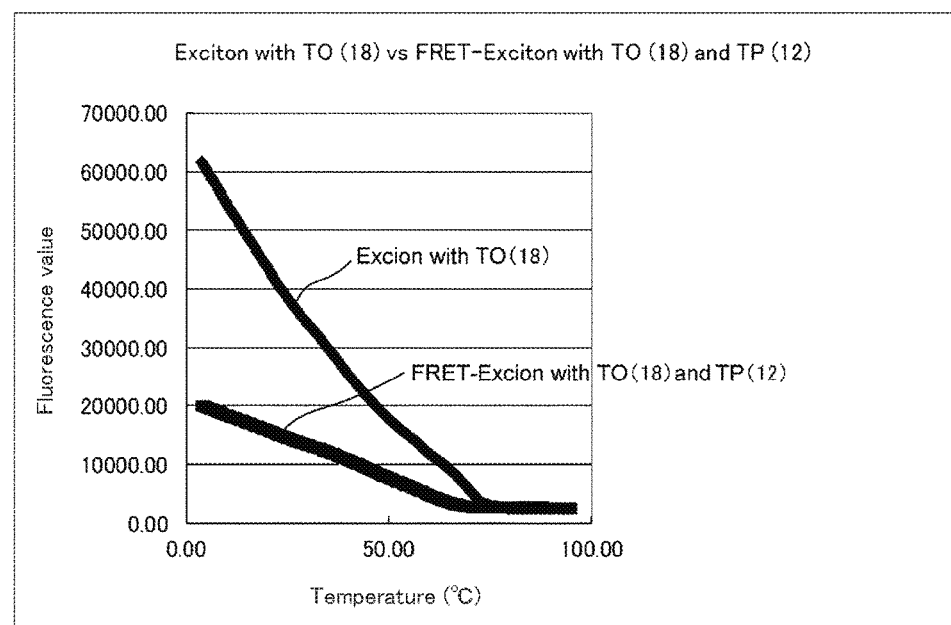
FIG. 2E shows a result of melting curve analysis of a fluorescence nucleic acid probe (EX18-12TOTP) into which two fluorescent dyes having an exciton effect have been introduced, obtained in Example 1 (the distance between thiazole orange (TO, at 18th base from the 3' end) and thiazole pink (TP, at the 12th base from the 3' end): 8 bases). As a comparison, the result of melting curve analysis of a fluorescence nucleic acid probe into which only thiazole orange (TO) has been introduced into the same position is shown.

The probes were excited at an excitation wavelength (490 nm) of thiazole orange to carry out spectrum measurement. The spectrum measurement was carried out using a fluorescence measurement device (RF5300) manufactured by Shimadzu Corporation. The measurement was carried out at concentrations of each fluorescence probe and a complementary strand (SEQ ID NO: 2) of 1 μM and a temperature of 23° C. The results are shown in FIGS. 1A to 1C. FIG. 1A is a spectrum obtained in the case of using a fluorescence nucleic acid probe into which two fluorescent dyes having an exciton effect have been introduced. FIGS. 1B and 1C are spectra of a conventional fluorescence probe having an exciton effect. In the case of two fluorescent dyes having an exciton effect, the fluorescence at a wavelength (601 nm) of thiazole pink caused by the FRET effect could be observed. At that time, the ratio (S/N ratio) between the signal intensity in the single strand state (background) and the signal intensity in the double strand state (in measurement) was 4.6. In the case of introducing two fluorescent dyes having an exciton effect, the S/N ratio at a wavelength of an object to be measured was 4.6 which was two times or more improved compared with the case of one fluorescent dye (FIG. 1B: S/N=2.1, FIG. 1C: S/N=1.8).

This shows that, in the single strand state, the fluorescence energy of thiazole orange (533 nm) is inactivated to a certain extent by the exciton effect. However, when thiazole pink is present near the thiazole orange, the energy is received by the FRET effect, and at the same time, the energy is inactivated by the exciton effect.

Example 3

Melting curve analysis of the fluorescence nucleic acid probe into which two fluorescent dyes having exciton effect had been introduced was carried out using a real-time PCR device (CFX96) manufactured by BioRad. The measurement of the melting curve was carried out at concentrations of each fluorescence probe and a complementary strand of 1 µM and a volume of 25 µl. The measurement was carried out while increasing the temperature from 4° C. to 95° C. by 0.5° C. The results are shown in FIGS. 2A to 2E. The results shown in FIGS. 2A to 2E are comparison of fluorescence of thiazole orange (excitation wavelength: 495 nm). When the distance between thiazole orange and thiazole pink is appropriate, the fluorescence of thiazole orange was largely reduced by the FRET effect.

It is considered from the results in FIGS. 2A to 2E that the FRET effect is most exhibited in the fluorescence labeled single-stranded nucleic acid (DNA) used in the present example when the distance between two fluorescent dyes having an exciton effect is about 3 bases excluding the fluorescent dyes. It is found that when the distance is too short (one base excusing the fluorescent dyes) or too long (five bases excluding the fluorescent dyes), the FRET effect becomes low. The base sequences of the fluorescence nucleic acid probes used to obtain the results of the melting curve analysis shown in FIGS. 2A to 2E are as follows.

INDUSTRIAL APPLICABILITY

The present invention is useful in a field using a fluorescence labeled probe or primer.

SEQUENCE LISTING

SEQ ID NO: 1: a base sequence of oligo DNA strand (20 mer) synthesized in Example 1
SEQ ID NO: 2: a base sequence of complementary strand of oligo DNA strand (20 mer) synthesized in Example 1

The invention claimed is:

1. A labeled single-stranded nucleic acid comprising at least two fluorescent atomic group pairs that exhibit an exciton effect within each fluorescent atomic group pair, wherein an emission peak wavelength of a fluorescent atomic group pair J is shorter than an excitation peak wavelength of a fluorescent atomic group pair K, the fluorescent atomic group pair J and the fluorescent atomic group pair K are both cations, the fluorescent atomic group pairs J and K have a Förster resonance energy transfer (FRET) effect between each other, each of a base having the fluorescent atomic group pair J or K that exhibits an exciton effect has a structure represented by the following formula (16), (16b), (17), or (17b):

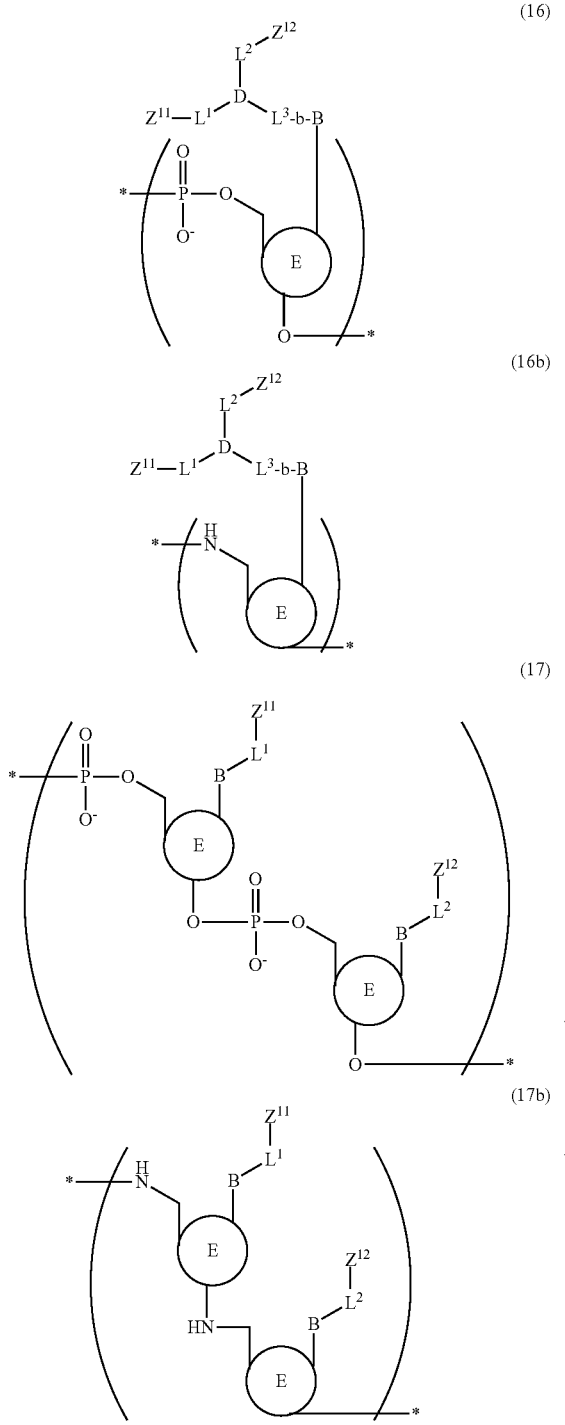

where in the formulae (16), (16b), (17), and (17b), $Z^{11}$ and $Z^{12}$ are each a fluorescent atomic group that exhibits an exciton effect, and may be identical to or different from each other, $Z^{11}$ and $Z^{12}$ constitute a fluorescent atomic group pair, B is an atomic group having a natural nucleobase skeleton or an artificial nucleobase skeleton, wherein the natural nucleobase is adenine, guanine, cytosine, thymine or uracil, E is:
(i) an atomic group having a deoxyribose skeleton, a ribose skeleton, or a structure derived from either one of them, or
(ii) an atomic group having a peptide structure or a peptoid structure, $L^1$, $L^2$, and $L^3$ are each a linking atom or a linking atomic group, having any number of main chain atoms, each may or may not contain each of C, N, O, S, P, and Si in the main chain, each may or may not contain each of a single bond, a double bond, a triple bond, an amide bond, an ester bond, a disulfide bond, an imino group, an ether bond, a thioether bond, and a thioester bond in the main chain, and may be identical to or different from each other, D is CR, N, P, P═O, B, or SiR where R is a hydrogen atom, an alkyl group, or any substituent, and b is a single bond, a double bond, or a triple bond, or alternatively, in the formulae (16) and (16b), $L^1$- and $L^2$ are each a linker, $L^3$, D, and b may not be present, and $L^1$ and $L^2$ may be bound directly to B, provided that:

in the formulae (16) and (17), E is an atomic group described in the item (i), and at least one O atom in a phosphoric acid linkage may be substituted with an S atom;

in the formulae (16b) and (17b), E is an atomic group described in the item (ii);

in the formulae (17) and (17b), the respective Bs may be identical to or different from each other, and the respective Es may be identical to or different from each other; and the base having the fluorescent atomic group pair J and the base having the fluorescent atomic group pair K are contained in the labeled single-stranded nucleic acid at a distance at which there are from 1 to 5 bases between the base having the fluorescent atomic group pair J and the base having the fluorescent atomic group pair K.

2. The labeled single-stranded nucleic acid according to claim 1, wherein the base having the fluorescent atomic group pair J and the base having the fluorescent atomic group pair K are contained in the labeled single-stranded nucleic acid at a distance at which the fluorescent atomic group pairs J and K have an FRET effect between each other.

3. The labeled single-stranded nucleic acid according to claim 1, wherein the structure represented by the formula (16) is a structure represented by the following formula (16-1) or (16-2), the structure represented by the formula (16b) is a structure represented by the following formula (16b-1) or (16b-2), the structure represented by the formula (17) is a structure represented by the following formula (17-1), and the structure represented by the formula (17b) is a structure represented by the following formula (17b-1):

(16-1)

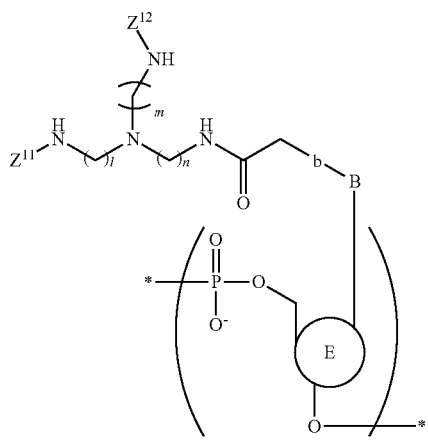

(16-2)

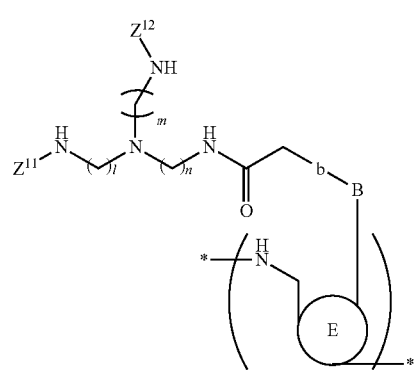

(16b-1)

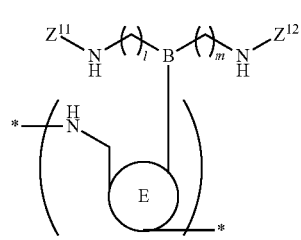

(16b-2)

(17-1)

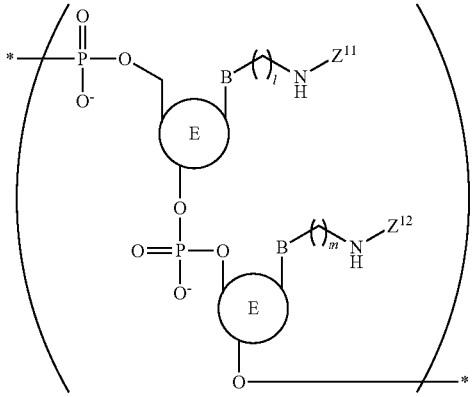

(17b-1)

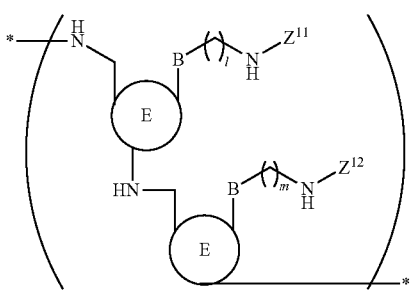

where in the formulae (16-1), (16-2), (16b-1), (16b-2), (17-1), and (17b-1), l, m and n are any positive integers, may be identical to or different from each other, each may or may not contain each of C, N, O, S, P, and Si in a main chain thereof, and each may or may not contain each of a single bond, a double bond, a triple bond, an amide bond, an ester bond, a disulfide bond, an imino group, an ether bond, a thioether bond, and a thioester bond in the main chain, $B, E, Z^{11}, Z^{12}$, and b are identical to those in the formulae (16), (16b), (17), and (17b), and in the formulae (16-1), (16-2), and (17-1), at least one O atom in a phosphoric acid linkage may be substituted with an S atom.

4. The labeled single-stranded nucleic acid according to claim 1, wherein the base having the fluorescent atomic group pair that exhibits an exciton effect has a structure represented by the formula (16).

5. The labeled single-stranded nucleic acid according to claim 1, wherein $Z^{11}$ and $Z^{12}$ are each independently an atomic group represented by any one of the following formulae (7) to (10):

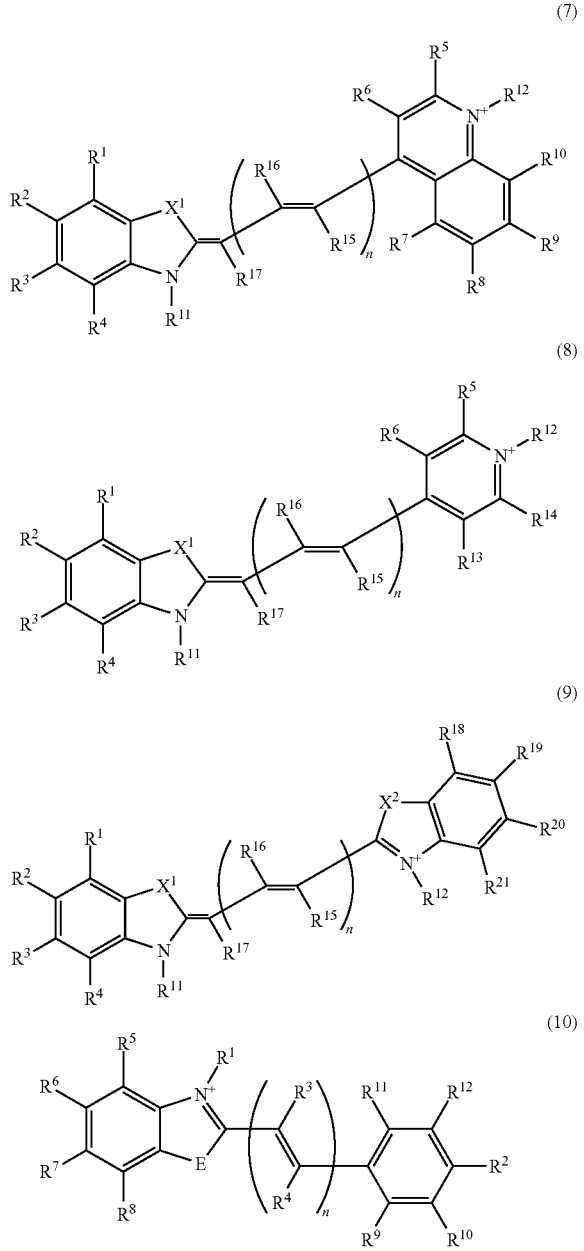

(7)

(8)

(9)

(10)

where in the formulae (7) to (9),
X$^1$ and X$^2$ are S or O
n is 0 or a positive integer,
R$^1$ to R$^{10}$ and R$^{13}$ to R$^{21}$ are each independently a hydrogen atom, a halogen atom, a lower alkyl group, a lower alkoxy group, a nitro group, or an amino group,
one of R$^{11}$ and R$^{12}$ is a linking group to be bound to L$^1$- or L$^2$ in the formulae (16), (17), (16b), and (17b), and the other is a hydrogen atom or a lower alkyl group,
when a plurality of R$^{15}$s are present in the formula (7), (8), or (9), they may be identical to or different from each other,
when a plurality of R$^{16}$s are present in the formula (7), (8), or (9), they may be identical to or different from each other, and
X$^1$, X$^2$, and R$^1$ to R$^{21}$ in Z$^{11}$ and X$^1$, X$^2$, and R$^1$ to R$^{21}$ in Z$^{12}$ may be identical to or different from each other, respectively, and where in the formula (10),
E is S or O,
R$^2$ to R$^{12}$ are each independently a hydrogen atom, a halogen atom, a lower alkyl group, a lower alkoxy group, a nitro group, or an amino group,
R$^1$ is a linking group to be bound to L$^1$ or L$^2$ in the formulae (16), (17), (16b), and (17b),
when a plurality of R$^3$s is present in the formula (10), they may be identical to or different from each other, and
when a plurality of R$^4$s is present in the formula (10), they may be identical to or different from each other.

6. The labeled single-stranded nucleic acid according to claim 5, wherein
Z$^{11}$ and Z$^{12}$ are each independently an atomic group represented by the formula (7) or (8), and
Z$^{11}$ and Z$^{12}$ represented by the formula (7) or (8) are each a group represented by the following formula (19) or (20):

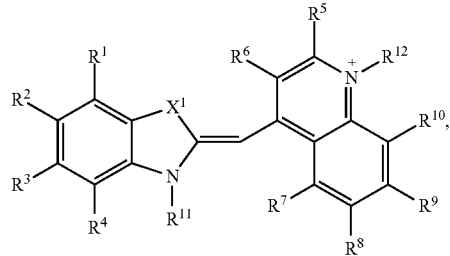

(19)

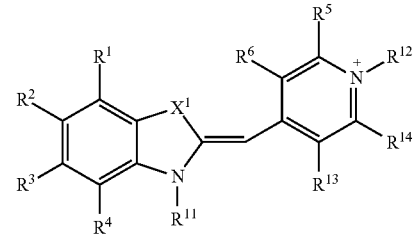

(20)

where in the formulae (19) and (20),
X$^1$, R$^1$ to R$^{10}$, R$^{13}$ and R$^{14}$, R$^{11}$, and R$^{12}$ are identical to those in the formulae (7) to (9).

7. The labeled single-stranded nucleic acid according to claim 1, used as a primer for amplifying a target nucleic acid or a probe to be hybridized with a target nucleic acid.

8. A method for detecting a target nucleic acid, comprising measuring fluorescence under the conditions where the labeled single-stranded nucleic acid according to claim 1 as a probe is capable of hybridizing with a target nucleic acid, to determine the presence or absence of the hybridization of the target nucleic acid to the probe.

9. A method for amplifying a target nucleic acid, comprising amplifying a target nucleic acid using the labeled single-stranded nucleic acid according to claim 1 as a primer.

* * * * *

```
SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: synthesized oligo DNA sequence

<400> SEQUENCE: 1
tgtgtatctt tctctttctc                                                     20

<210> SEQ ID NO 2
<211> LENGTH: 20
<212> TYPE: DNA
<213> ORGANISM: Artificial Sequence
<220> FEATURE:
<223> OTHER INFORMATION: synthesized oligo DNA sequence

<400> SEQUENCE: 2
gagaaagaga aagatacaca                                                     20
```